United States Patent [19]

Summerton et al.

[11] Patent Number: 5,034,506
[45] Date of Patent: Jul. 23, 1991

[54] UNCHARGED MORPHOLINO-BASED POLYMERS HAVING ACHIRAL INTERSUBUNIT LINKAGES

[75] Inventors: James E. Summerton; Dwight D. Weller, both of Corvallis, Oreg.

[73] Assignee: Anti-Gene Development Group, Corvallis, Oreg.

[21] Appl. No.: 454,055

[22] Filed: Dec. 20, 1989

Related U.S. Application Data

[63] Continuation-in-part of Ser. No. 100,033, Sep. 23, 1987, which is a continuation-in-part of Ser. No. 944,707, Dec. 18, 1986, and a continuation-in-part of Ser. No. 911,258, Nov. 25, 1986, abandoned, and a continuation-in-part of Ser. No. 712,396, Mar. 15, 1985, abandoned.

[51] Int. Cl.$^5$ .................... C08G 75/18; C08G 75/20; C08G 75/24
[52] U.S. Cl. .................... 528/391; 528/403; 528/405; 528/406
[58] Field of Search .............. 528/391, 403, 405, 406

[56] References Cited

FOREIGN PATENT DOCUMENTS 63-303341 12/1988 Japan.

OTHER PUBLICATIONS

CA 112 (13): 119320a Stirchak, E. P. "Uncharged Stereo Regular Nucleic Acid Analogs," *Nucleic Acids Res.*, vol. 17, No. 15, 1989.
CA 110 (22): 202954q Terada, Kazutoshi et al. "Photosensitive Compositions for Printing Plates".
CA 75 (7): 48222z Belikov, V. et al., "Effect of the Polarity of Substituents on the Decomposition Rate of Beta.-Nitroamines," *Inst. Elementoorg. Soedin,* 1971.

Khym, J. X., Biochemistry 2 (2):334 (1963).
Mungall, W. S. et al., J. Org. Chem. 42 (4):703 (1977).
Tittensor, J. R., J. Chem. Soc. (C):2656 (1971).
Gait, M. J. et al., J. C. S. Perkins I:1684 (1974).
Jones, A. S. et al., Biochem. et Biphys. Acta 365:365 (1973).
Blake et al., Biochem. 24:6132 (1985a).
Blake et al., Biochem. 24:6139 (1985b).
Froehler et al., Nucleic Acids Res. 16:4831 (1988).
Jayaraman et al., Proc Natl Acad Sci U.S.A. 78:1537 (1981).
Miller et al., Biochemistry 18:5134 (1979).
Miller et al., J. Biol. Chem. 255:6959 (1980).
Miller et al., Biochimie 67:769 (1985).
Murakami et al., Biochemistry 24:4041 (1985).
Pitha, Biochem Biphys Acta 204:39 (1970a).
Pitha, Biopolymers 9:965 (1970b).
Smith et al., Proc. Natl. Acad. Sci. U.S.A. 83:2787 (1986).
Stirchak, E. P. et al., Organic Chem. 52:4202 (1987).

*Primary Examiner*—Harold D. Anderson
*Assistant Examiner*—T. Mosley
*Attorney, Agent, or Firm*—Peter J. Dehlinger; Gary R. Fabian

[57] ABSTRACT

A polymer composition is disclosed composed of morpholino subunit structures which are linked together by uncharged, achiral linkages. These linkages are one to three atoms in length, joining the morpholino nitrogen of one subunit to the 5' exocyclic carbon of an adjacent subunit. Each subunit contains a purine or pyrimidine base-pairing moiety effective to bind by hydrogen bonding to a specific base or base-pair in a target polynucleotide.

13 Claims, 17 Drawing Sheets

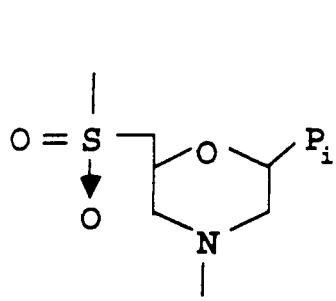 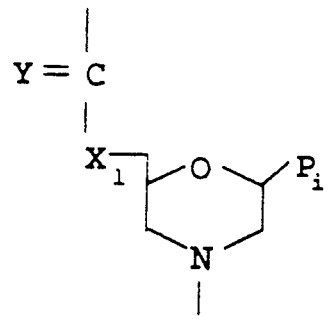 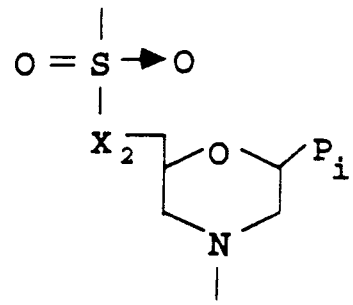
Fig. 3A  Fig. 3B  Fig. 3C
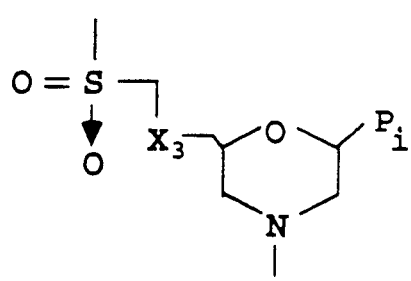 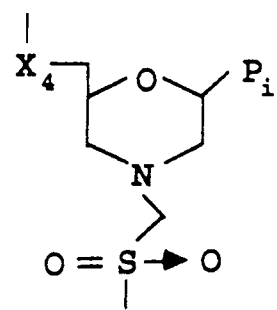
Fig. 3D  Fig. 3E
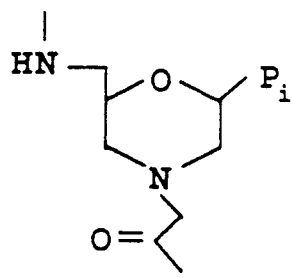 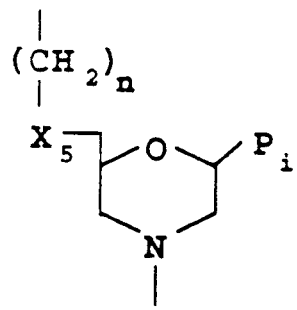
Fig. 3F  Fig. 3G

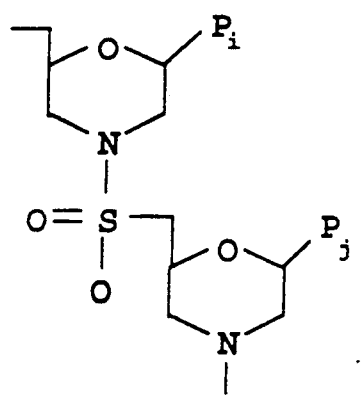
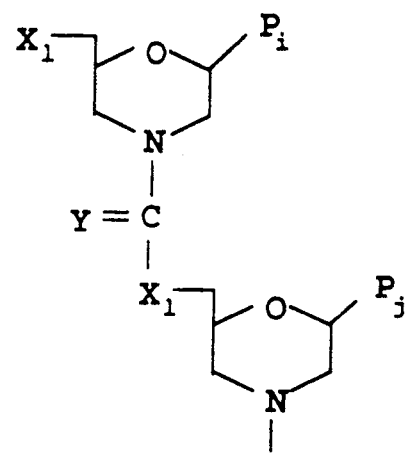
Fig. 4A-A
Fig. 4B-B
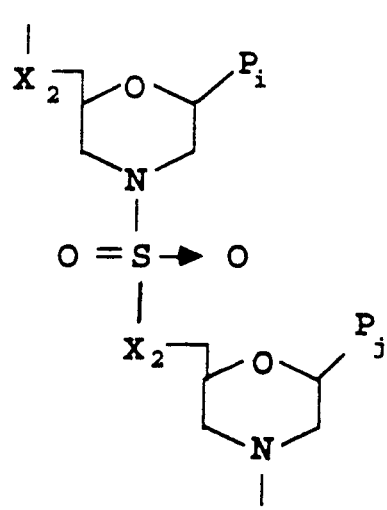
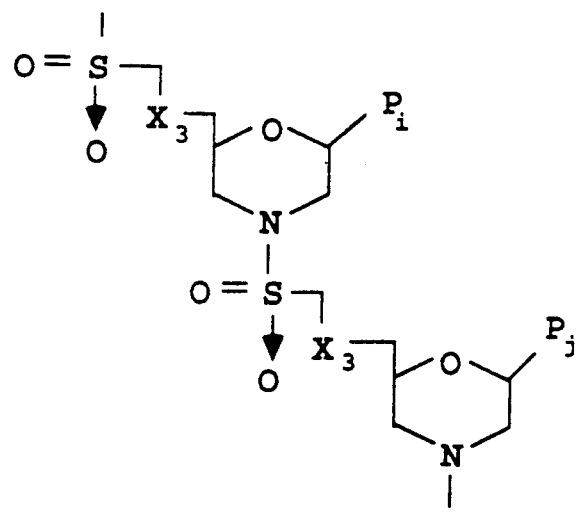
Fig. 4C-C
Fig. 4D-D

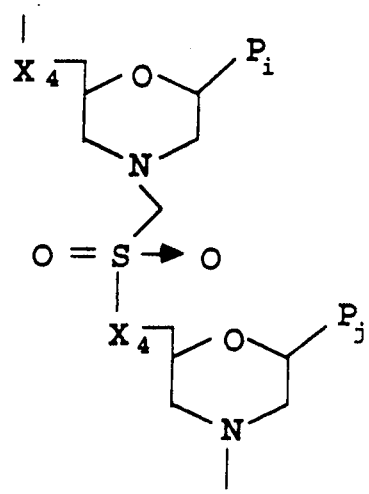
Fig. 4E-E
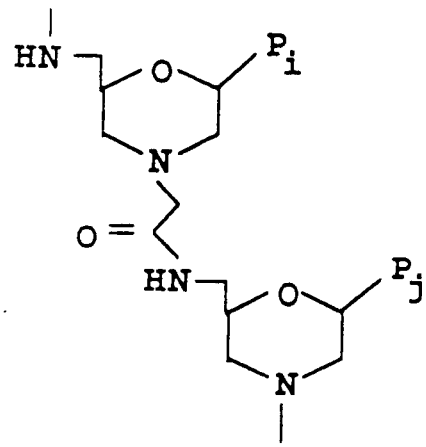
Fig. 4F-F
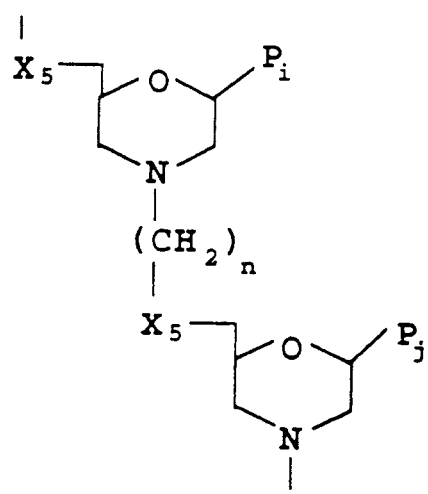
Fig. 4G-G

Fig. 5 (con't)
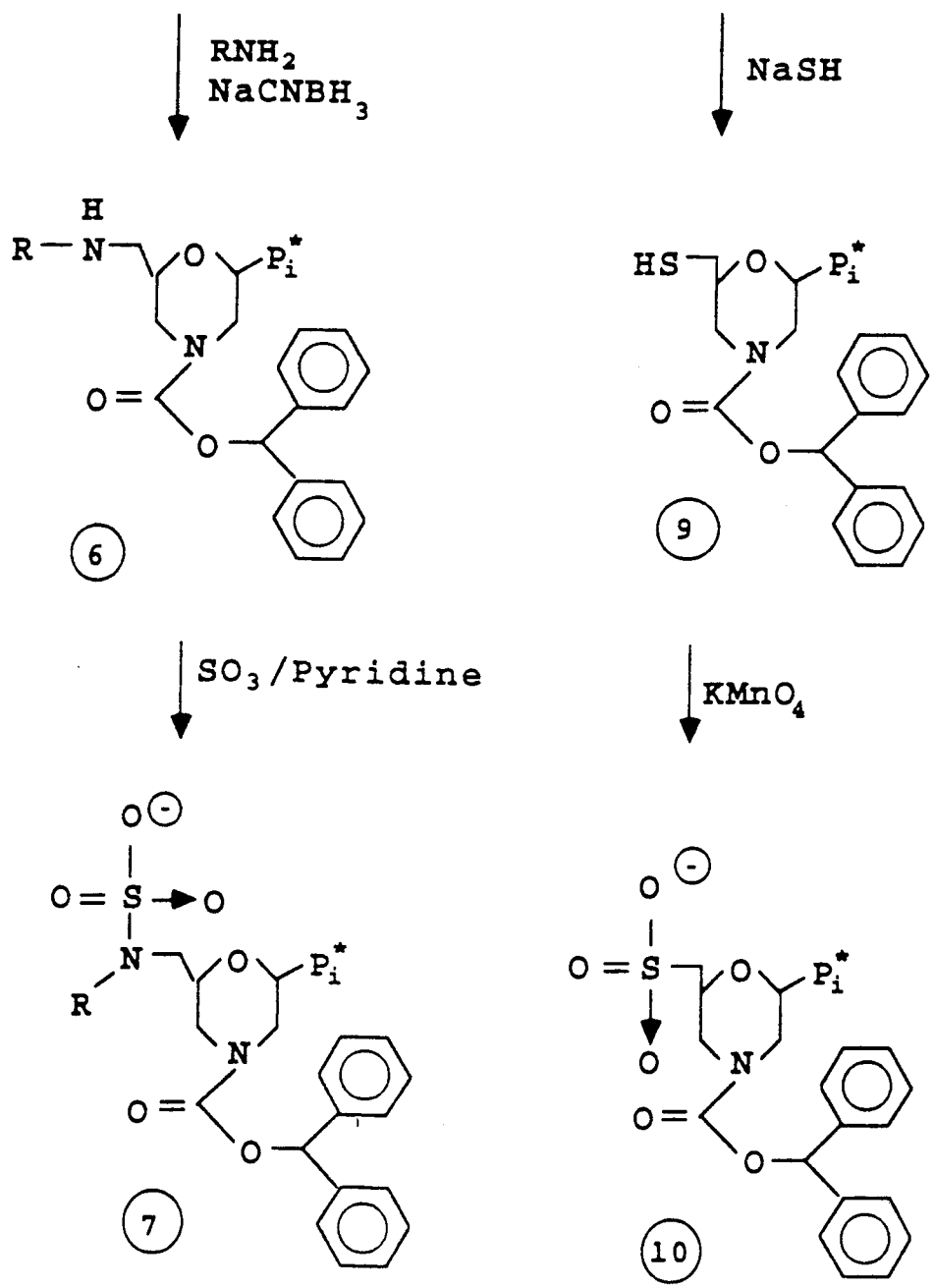

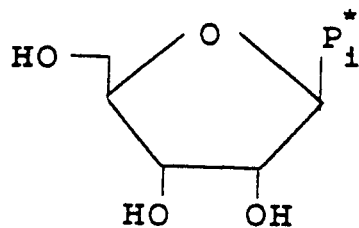
Fig. 6
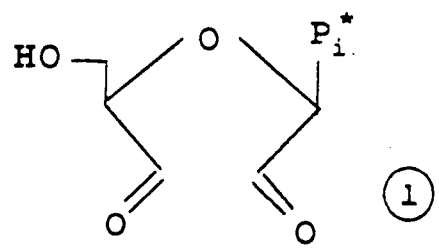
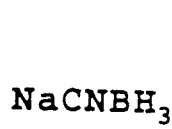
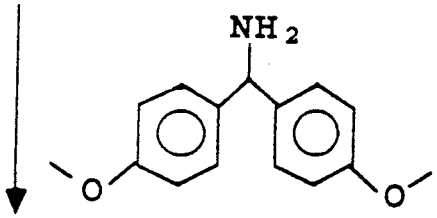
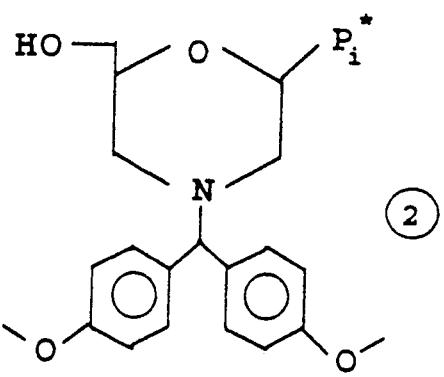

```
5'  GGDDDGDDGucDGDDGGcDDDDD    polymer
    ||||||||||::||||||:|||||
5'  ggaaagaagtcagaaggcaaaaa    target
3'  cctttcttcagtcttccgttttt    duplex
```

| = High Specificity Hydrogen Bonding

: = Low Specificity Hydrogen Bonding

UNCHARGED MORPHOLINO-BASED POLYMERS HAVING ACHIRAL INTERSUBUNIT LINKAGES

This application is a continuation-in-part (CIP) of co-pending U.S. Pat. Application Ser. No. 07/200,033 filed Sept. 23, 1987. Application Ser. No. 07/100,033 is a CIP of pending U.S. Pat. Application Ser. No. 06/944,707, filed Dec. 18, 1986 and a CIP of 06/911,258, filed Nov. 25, 1986 now abandoned, and a CIP of 06/712,396, filed Mar. 15, 1985, now abandoned.

This application was filed on even date with co-pending U.S. Pat. Applications Ser. Nos. 07/454,057 and 07/454,056.

FIELD OF THE INVENTION

The present invention relates to morpholino-based polymers.

REFERENCES

Agarwal, Proc Nat Acad Sci USA, 85:7079 (1988).
Balgobin, N., et al., Tetrahedron Lett, 22:3667 (1981).
Belikova, Tetrahedron Lett, 37:3557 (1967).
Blake et al., Biochem, 24:6132 (1985a).
Blake et al., Biochem 24:6139 (1985b).
Dikshit et al., Canadian J Chem, 66:2989 (1988).
Fild et al., Chem Ber, 113:142 (1980).
Froehler, et al., Nucleic Acids Res. 16:4831 (1988).
Fox, J.J., et al., J Am Chem Soc, 80:1669 (1958).
Gait, "Oligonucleotide Synthesis, A practical Approach," pages 31-33, IRL Press, Oxford, England (1984).
Goldberg, M. L. et al; Methods in Enzymology 68:206 (1979).
Greenlee, J Org Chem, 49 2632 (1984).
Grunstein, M. et al; Methods in Enzymology 68:379 (1979).
Himmelsbach, F., and W. Pfleiderer, Tetrahedron Lett, 24:3583 (1983).
Jayaraman, et al., Proc Natl Acad Sci USA 78:1537 (1981).
Kamimura et al., Chemistry Letters (The Chem. Soc. of Japan) pg. 1051 (1983).
Lerman, L.S., "DNA Probes: Applications in Genetic and Infectious Disease and Cancer," Current Comm in Molec Biol, Cold Spring Harbor Laboratory (1986).
Letsinger and Miller, J Amer Chem Soc, 91:3356 (1969).
McBride et al., J Amer Chem Soc 108:2040 (1986).
Miller, et al., Biochemistry 18:5134 (1979).
Miller, et al., J Biol Chem 255:6959 (1980).
Miller, et al., Biochimie 67:769 (1985).
Murakami, et al., Biochemistry 24:4041 (1985).
Niedballa, U., and H. Vorbruggen, J Org Chem, 39:3668 (1974).
Pitha, Biochem Biophys Acta 204:39 (1970a).
Pitha, Biopolymers 9:965 (1970b).
Reese, C.B., and R.S. Saffhill, J Chem Soc Perkin Trans, 1:2937 (1972).
Smith, et al., J Amer Chem Soc 80:6204 (1958).
Smith, et al., Proc Natl Acad Sci USA 83:2787 (1986).
Southern, E.; Methods in Enzymology 68:152 (1979)
Stirchak E.P. et al., Organic Chem. 52:4202 (1987).
Summerton, et al., J Molec Biol, 122:145 (1978).
Summerton, et al., J Theor Biol, 78:61 (1979a).
Summerton, J Theor Biol, 78:77 (1979b).
Szostak, J. W. et al; Methods in Enzymology 68:419 (1979).
Thomas, P.; Methods in Enzymology 100:255 (1983).
Toulme et al., Proc Nat Acad Sci, USA 83:1227 (1986).
Trichtinger et al., Tetrahedron Letters 24:711 (1983).

BACKGROUND OF THE INVENTION

Polymers which are designed for base-specific binding to polynucleotides have significant potential both for in vitro detection of specific genetic sequences characteristic of pathogens (Lerman) and for in vivo inactivation of gene tic sequences causing many diseases—particularly viral diseases (Belikova, Summerton).

Standard ribo- and deoxyribonucleotide polymers have been widely used both for detection of complementary genetic sequences, and more recently, for inactivating targeted genetic sequences. However, standard polynucleotides suffer from a number of limitations when used for base-specific binding to target oligonucleotides. These limitations include (i) restricted passage across biological membranes, (ii) nuclease sensitivity, (iii) target binding which is sensitive to ionic concentration, and (iv) susceptibility to cellular strand-separating mechanisms.

In principle, the above limitations can be overcome or minimized by designing polynucleic acid analogs in which the bases are linked along an uncharged backbone. Examples of uncharged nucleic acid analogs have been reported. Pitha et al (1970a, b) have disclosed a variety of homopolymeric polynucleotide analogs in which the normal sugar-phosphate backbone of nucleic acids is replaced by a polyvinyl backbone. These nucleic acid analogs were reported to have the expected Watson/Crick pairing specificities with complementary polynucleotides, but with substantially reduced Tm values (Pitha, 1970a). One serious limitation of this approach is the inability to construct polymers by sequential subunit addition, for producing polymers with a desired base sequence. Thus the polymers cannot be used for base-specific binding to selected target sequences. Polynucleotide analogs containing uncharged, but stereoisomeric, methylphosphonate linkages between the deoxyribonucleoside subunits have been reported (Miller, 1979, 1980; Jayaraman; Murakami; Blake, 1985a, 1985b; Smith). More recently a variety of analogous uncharged phosphoramidate-linked oligonucleotide analogs have also been reported (Froehler, 1988). These polymers comprise deoxynucleosides linked by the 3'OH group of one subunit and the 5' OH group of another subunit via an uncharged chiral phosphorous-containing group. These compounds have been shown to bind to and selectively block single-strand polynucleotide target sequences. However, uncharged phosphorous-linked polynucleotide analogs of the type just described have limitations, particularly the cost and difficulty of preparing the polymers.

More recently, deoxyribonucleotide analogs having uncharged and achiral intersubunit linkages have been constructed (Stirchak 1987). Since these polymers are stereo-regular, all polymers having a given subunit sequence will have the same Tm value for a given target nucleotide sequence, thus avoiding some of the limitations inherent in chirally-linked polymers. These uncharged, achiral deoxyribonucleoside-derived analogs, however, are limited by relatively high cost of starting materials.

SUMMARY OF THE INVENTION

It is therefore one general object of the invention to provide a polymer capable of sequence-specific binding to polynucleotides and which overcomes or minimizes many of the problems and limitations associated with polynucleotide analog polymers noted above.

The invention includes a polymer composition containing morpholino ring structures of the form:

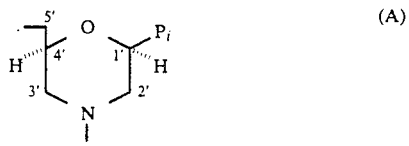

(A)

The ring structures are linked together by uncharged, achiral linkages, one to three atoms long, joining the morpholino nitrogen of one ring structure to the 5' exocyclic carbon of an adjacent ring structure.

Each ring structure includes a purine or pyrimidine base-pairing moiety ($P_i$) which is effective to bind by base-specific hydrogen bonding to a base in a target sequence in a polynucleotide.

These and other objects and features of the invention will become more fully apparent when the following detailed description of the invention is read in conjunction with the accompanying examples and figures.

BRIEF DESCRIPTION OF THE FIGURES

FIG. 3 shows several preferred subunits having 5-atom (A), six-atom (B and C) and seven-atom (D-G) linking groups suitable for forming polymers. Y = O or S. $X_1$ = O or S $X_2$ O, S, $CH_2$, or $NR_1$. $X_3$ = O, S, $CH_2$, or $NR_2$. $X_4$ = O, S, or $NR_1$. $X_5$ = O, S, $CH_2$, $NR_{2'}$, or $SO_2$. n = 0, 1, or 2; when n = 0, $X_5$ is not $SO_2$. When n = 1, $X_5$ is $CH_2$ or $SO_2$. $R_1$ = H, $CH_3$, or other group which does not interfere with sequence-specific hydrogen-bonding of the polymer to its target polynucleotide. $R_2$ is an electron withdrawing group, such as methanesulfonyl, which reduces the pKa of the nitrogen to which it is attached to less than pKa=6.

FIG. 4 shows a repeating subunit segment of exemplary morpholino-based polymers, designated A—A through G—G, constructed using subunits A-G, respectively, of FIG. 3. Y, $X_1$, $X_2$, $X_3$, $X_4$, $X_5$, n, $R_1$, and $R_2$ are as in FIG. 3.

FIG. 6 shows an alternative synthesis of the basic morpholino subunit.

FIG. 8 shows the binding mode for 2-amine-containing purines to polar major-groove sites of respective target base-pairs (FIG. 8a) and a representative base sequence of a duplex-binding polymer (FIG. 8b).

DETAILED DESCRIPTION OF THE INVENTION

The present invention includes a morpholino-based polymer which is designed for base-specific binding to a target sequence of a polynucleotide. The polymer is composed of morpholino-based ring structures which are linked together by uncharged, achiral linkages, one to three atoms long, joining the morpholino nitrogen of one structure to the 5' exocyclic carbon of an adjacent structure.

A. Morpholino-Based Subunits

Figure 1:
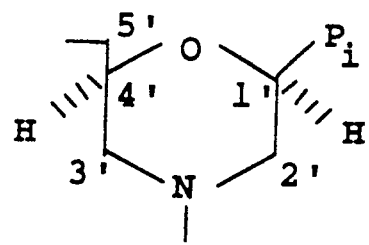
FIG. 1 shows a basic $\beta$-morpholino ring structure which is linked through uncharged, achiral linkages to form the polymer of the present invention. $P_i$ is a purine or pyrimidine base pairing moiety.

FIG. 1 shows the $\beta$-morpholino ring structures on which the polymer subunits are based, where the morpholino carbon atoms are numbered as in the parent ribose. As seen in FIG. 1, the ring structure contains a 5' methylene attached to the 4' carbon in the $\beta$-orientation.

Each ring structure includes a purine or pyrimidine or related hydrogen-bonding moiety, $P_i$, attached to the backbone morpholine moiety through a linkage in the $\beta$-orientation.

The purine hydrogen-bonding moieties or bases include purines as well as purine-like planar ring structures having a 5-6 fused ring in which one or more of the atoms, such as N3, N7, or N9 is replaced by a suitable atom, such as carbon. The pyrimidine moieties likewise include pyrimidines as well as pyrimidine-like planar 6-membered rings in which one or more of the atoms, such as N1, is replaced by a suitable atom, such as carbon. Preferred hydrogen-bonding moieties in the invention include the set of purines and pyrimidines shown in FIG. 2. Each base includes at least two hydrogen-bonding sites specific for a polynucleotide base or base-pair. Where the polymers are used for sequence-specific binding to single-stranded polynucleotides, the purine structures 1-3 are designed to bind to thymine or uracil bases; structures 7-8, to guanine bases; structures 4-6, to cytosine bases; and structure 9, to adenine bases.

The polymers of the invention are also effective to bind to hydrogen-bonding sites accessible through the major-groove in duplex polynucleotides having mostly purine bases in one strand and mostly pyrimidine bases in the complementary strand, as discussed below.

Figure 2:
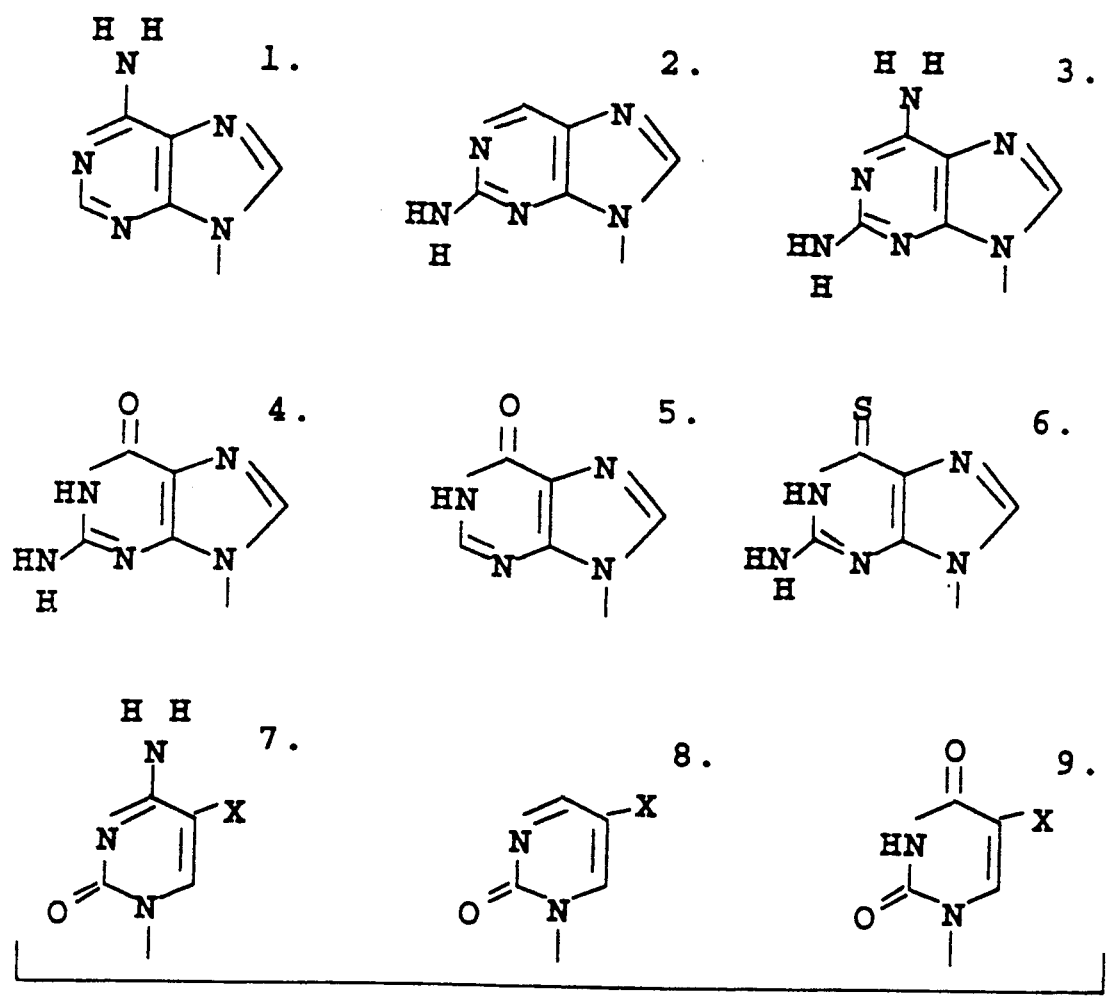
FIG. 2 shows several exemplary purine- and pyrimidine base-pairing moieties (represented as Pi of the ring structures shown in FIG. 1), where X = H, CH3, F, Cl, Br, or I.

Because of the similar type and positioning of the two central polar major-groove sites among the different base-pairs of duplex nucleic acids (i.e., the NH4 and O6 of a CG base-pair present the same H-bonding array as the NH6 and O4 of an AT base-pair), the H-bonding moiety of a duplex-binding polymer must hydrogen-bond to the $N_7$ of its target base pair in order to uniquely recognize a given base-pair in a target genetic duplex. Thus, where the polymers of the present invention are targeted against duplex genetic sequences (containing predominantly purines in one strand and gen-bonding moieties of the polymer preferably contain purines having an amine at the 2 position since that amine is suitably positioned for H-bonding to the N7 of the target base-pair. Structures 2 and 3 of FIG. 2 provide for specific binding to a TA or UA base-pair, and Structures 4 and 6 provide for specific binding to a CG base-pair. Two bases which are particularly useful in a duplex-binding polymer are 2,6-diaminopurine (Structure 3) and guanine (Structure 4). FIG. 8 illustrates the binding of these two bases to the polar major-groove sites of their respective target base-pairs in duplex nucleic acids.

The morpholino subunits of the instant invention are combined to form polymers by linking the subunits through stable, achiral, uncharged linkages. The linking group of a subunit usually includes a carbonyl or sulfonyl electrophile for reaction with a nucleophile of the subunit to which it is to be linked. As used herein "carbonyl" means a 13 C=O or —C=S group, and "sulfonyl" means an O=S→O group.

The selection of subunit linking groups for use in polymer synthesis is guided by several considerations. Initial screening of promising intersubunit linkages (i.e., those linkages which are predicted to not be unstable and which allow either free rotation about the linkage or which exist in a single conformation) typically involves the use of space-filling CPK or computer molecular models of duplex DNA or RNA. The DNA and RNA duplexes are constructed according to parameters determined by x-ray diffraction of oligodeoxyribonucleotides in the B-form and oligoribonucleotide-containing duplexes in the A-form.

In each of these constructed duplexes, one of the two sugar phosphate backbones is removed, and the prospective backbone, including the morpholino ring and intersubunit linkage, is replaced, if possible, on the sites of the bases from which the original sugar-phosphate backbone has been removed. Each resulting polynucleotide/polymer duplex is then examined for coplanarity of the Watson/Crick base pairs, torsional and angle strain in the prospective binding polymer backbone, degree of distortion imposed on the nucleic acid strand, and interstrand and intrastrand nonbonded interactions.

In the case of amide-containing linkages, special attention is paid to whether or not amide-containing backbones can readily adopt a conformation in which the amide moieties are planar. This is important because of the substantial energy cost required to force an amide into a nonplanar conformation.

Initial studies of this type carried out in support of the present invention showed that for morpholino-based polymers the preferred unit backbone length (i.e., the number of atoms in a repeating backbone chain in the polymer) is 6 atoms. However, the modeling studies also show that certain 5-atom and 7-atom repeating-unit morpholino-based backbones meet the requirements for binding to targeted genetic sequences.

Since the morpholino structure itself contributes 4 atoms to each repeating backbone unit, the linkages in the five-atom, six-atom, and seven-atom repeating-unit backbone contribute one, two, and three atoms to the backbone length, respectively. In all cases, the linkage between the ring structures is (a) uncharged, (b) achiral, (c) stable, and (d) must permit adoption of a conformation suitable for binding to the target polynucleotide.

Subunit backbone structures judged acceptable in the above modeling studies were then assessed for feasibility of synthesis. The actual chemical stability of the intersubunit linkage was assessed with model compounds or dimers.

FIG. 3 shows several preferred $\beta$-morpholino subunit types, including linkage groups, which meet the constraints and requirements outlined above. It will be appreciated that a polymer may contain more than one linkage type.

Subunit A in FIG. 3 contains a 1-atom sulfonyl linkage which forms the five atom repeating-unit backbone shown at A—A in FIG. 4, where the morpholino rings are linked by a 1-atom sulfonamide linkage. It is noted here that the corresponding amide linkage (substituting a carbonyl for sulfonyl linkage) is not acceptable due to lack of rotational freedom about the carbon-nitrogen tertiary amide bond.

Subunits B and C in FIG. 3 are designed for 6-atom repeating-unit backbones, as shown at B—B and C—C, respectively, in FIG. 4. In Structure B, the atom X linking the 5' morpholino carbon to the carbonyl group may be oxygen or sulfur, but not nitrogen or carbon, due to lack of free rotation about the resultant intersubunit linkage. The C=Y carbonyl group may be either C=O or C=S, as noted above.

In Structure C, the moiety X linking the 5' morpholino carbon to the sulfonyl (O=S→O) group may be a methylene, oxygen, sulfur, or a nitrogen. The nitrogen may be secondary (NH), or tertiary (NR), where R is a methyl or other group which does not interfere with polymer binding to the target polynucleotide (as can be easily determined from molecular modeling studies such as those outlined above).

Subunits D-G in FIG. 3 are designed for 7-atom repeating-unit backbones, as shown at D—D through G—G, respectively, in FIG. 4. In Structure E, the X can be a secondary nitrogen (NH), or a tertiary nitrogen (NR) where R is a is a methyl or other group which does not interfere with polynmer binding to the target polynucleotide, as can be determined from molecular modeling studies. In addition, X in Structure E can be an oxygen since the 5' methylene in such morpholino structures is surprisingly resistant to nucleophilic attack.

Based on the molecular modeling studies of the type described above, both the sulfamate (Structure C—C of FIG. 4 wherein X is oxygen) and sulfonate (structure E—E of FIG. 4 wherein X is oxygen) linkages were good candidates. Experiments conducted in support of the present invention indicated that the 5' tosylate of the basic morpholino cytosine subunit (Structure 8 of FIG. 5, where Pi is N4-benzoylated cytosine) are surprisingly resistant to both intermolecular and intramolecular nucleophilic attack on the 5' methylene. This suggested that the corresponding sulfamate, and possibly the sulfonate also, may be sufficiently stable for intersubunit linkages. Accordingly, a sulfamate-linked dimer (Structure C—C of FIG. 4, where X is oxygen) was prepared, and assessed for linkage stability under conditions commonly used for polymer synthesis (i.e., detritylation conditions, base-deprotection conditions, and purification conditions, such as detailed in Example 19). These studies confirmed that such linkages are adequately stable under conditions typically required for synthesis, deprotection, purification and various applications.

In Structure G—G of FIG. 4, when n is zero, X must not be $SO_2$, and when n is one, X is $CH_2$, or $SO_2$.

B. Subunit Synthesis

The most economical starting materials for the synthesis of morpholino-subunits are generally ribonucleosides. Typically, ribonucleosides containing hydrogen-bonding moieties or bases (e.g., A, U, G, C) are transformed to their morpholino derivatives to provide a complete set of subunits for polymer synthesis. Where a suitable ribonucleoside is not available, a 1-haloribose or, preferably, a 1α-bromoglucose derivative, can be linked to a suitable base amd this nucleoside analog then converted to the desired β-morpholino structure via periodate cleavage, and closing the resultant dialdehyde on a suitable amine.

Because of the reactivity of the compounds used for subunit synthesis, activation, and/or coupling, it is generally desirable, and often necessary, to protect the exocyclic ring nitrogens of the bases and sometimes the oxygens of U and G. Selection of these protective groups is determined by (i) the relative reactivity of the moiety to be protected, (ii) the type of reactions involved in subunit synthesis and coupling, and (iii) the stability of the completed polymer prior to base deprotection.

Methods for base protecting a number of the more common ribonucleosides are given in Example 1. The methods detailed in the example are generally applicable for forming nucleosides with amine-protective groups. Standard base-protective groups used for nucleic acid chemistry are often suitable including the following groups: benzoyl for the N4 of cytosine (C); benzoyl or p-nitrobenzoyl for the N6 of adenine (A); acetyl, phenylacetyl or isobutyryl for the N2 of guanine (G); and N2,N6-bisisobutyryl for 2,6-diaminopurine residues. These protective groups can be removed after polymer assembly by treatment with ammonium hydroxide.

It is sometimes desirable to protect the base portion of the morpholino subunit with a group which can be readily removed by other than a nucleophilic base. Suitable base protective groups removable by a strong non-nucleophilic base via a β-elimination mechanism include: 2-(4-nitro-phenyl)ethoxy carbonyl or 2-(phenyl sulfonyl)ethoxycarbonyl for both the N4 of C and the N6 of A; and the 9-fluorenyl methoxycarbonyl for the N2 of G and the N2 and N6 of 2,6- diaminopurine. These groups can be removed after polymer assembly by treatment with the strong nonnucleophilic base 1,8-diazabicyclo[5.4.0]undec-7-ene (DBU), under stringently anhydrous conditions.

The syntheses of representative morpholino subunits follow here and are described in detail in Examples 2–10. With reference to the synthesis scheme depicted in FIG. 5, a base-protected ribonucleoside is reacted with sodium periodate to form a transient 2', 3'-dialdehyde which then closes upon ammonia to form a morpholino-ring having 2', and 3' hydroxyl groups (numbered as in the parent ribose, see FIG. 1). The compound is then treated with sodium cyanoborohydride to reduce the ring hydroxyl groups. The ring nitrogen is preferably protected by trityl derivatization or by a benzhydraloxycarbonyl group for subsequent subunit coupling. The protective group can be added by reacting the morpholino subunit with trityl chloride or with nitrophenyl benzhydryl carbonate or by reacting the dialdehyde with a primary amine, as illustrated in FIG. 6 and described in Example 3. The stereochemistry of the nucleoside starting material is retained as long as the pH of the reaction mixture at the iminium stage is not allowed to go above about 10.

The above synthesis results in a morpholino-ring with an available '-hydroxyl. The 5'-hydroxl can be converted to other active groups including ' amine (Example 5) and 5'-sulfonate (Example 6).

In the above morpholino synthesis a variety of nitrogen sources can be used —including ammonia, ammonium hydroxide, ammonium carbonate, and ammonium bicarbonate. Best results are obtained when the reaction solution is maintained near neutrality during the oxidation and morpholino ring closure reactions. This can be accomplished by continually titrating the reaction mix or, more conveniently, by using ammonium biborate as the ammonia source. When the solution is too acidic the yield of product is low and when it is too basic, side products (possibly due to epimerization of the 1' and/or 4' carbons) are produced which are difficult to separate from the desired product. It is also noted that the reducing agent can be added before, during, or after the oxidation step with little noticeable effect on product yield.

Ribonucleosides lacking base protection groups can also be successfully oxidized, ring closed, and reduced in aqueous solution to generate the morpholino ring. However, without base protection the number and quantity of undesired side products frequently increases, particularly in the case of cytidine.

Figure 5:
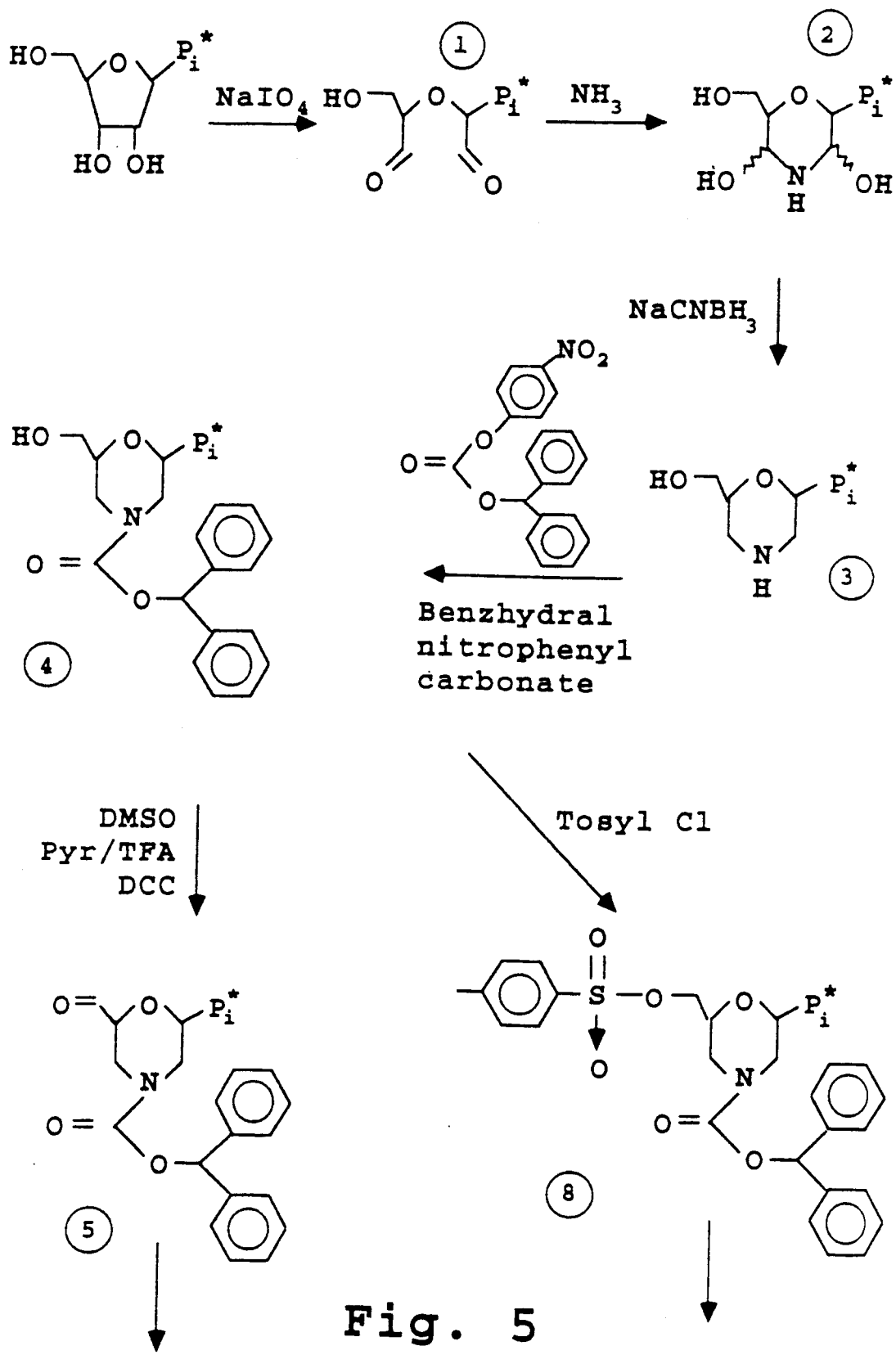
FIG. 5 shows the steps in the synthesis of several types of morpholino subunits from a ribonucleoside.

The subunits formed by the above methods contain a 5=-OH, SH, or amine which is modified, reacted with, and/or activated, to be suitable for coupling to a second morpholino subunit (see below). For example, FIG. 5 shows the conversion of a 5'-OH of a morpholino subunit to a sulfonyl linking moiety to form a subunit (Structure 10) which is linked to form a 5-atom unit-length backbone polymer. Details of the subunit synthesis are given in Example 6.

Figure 12:
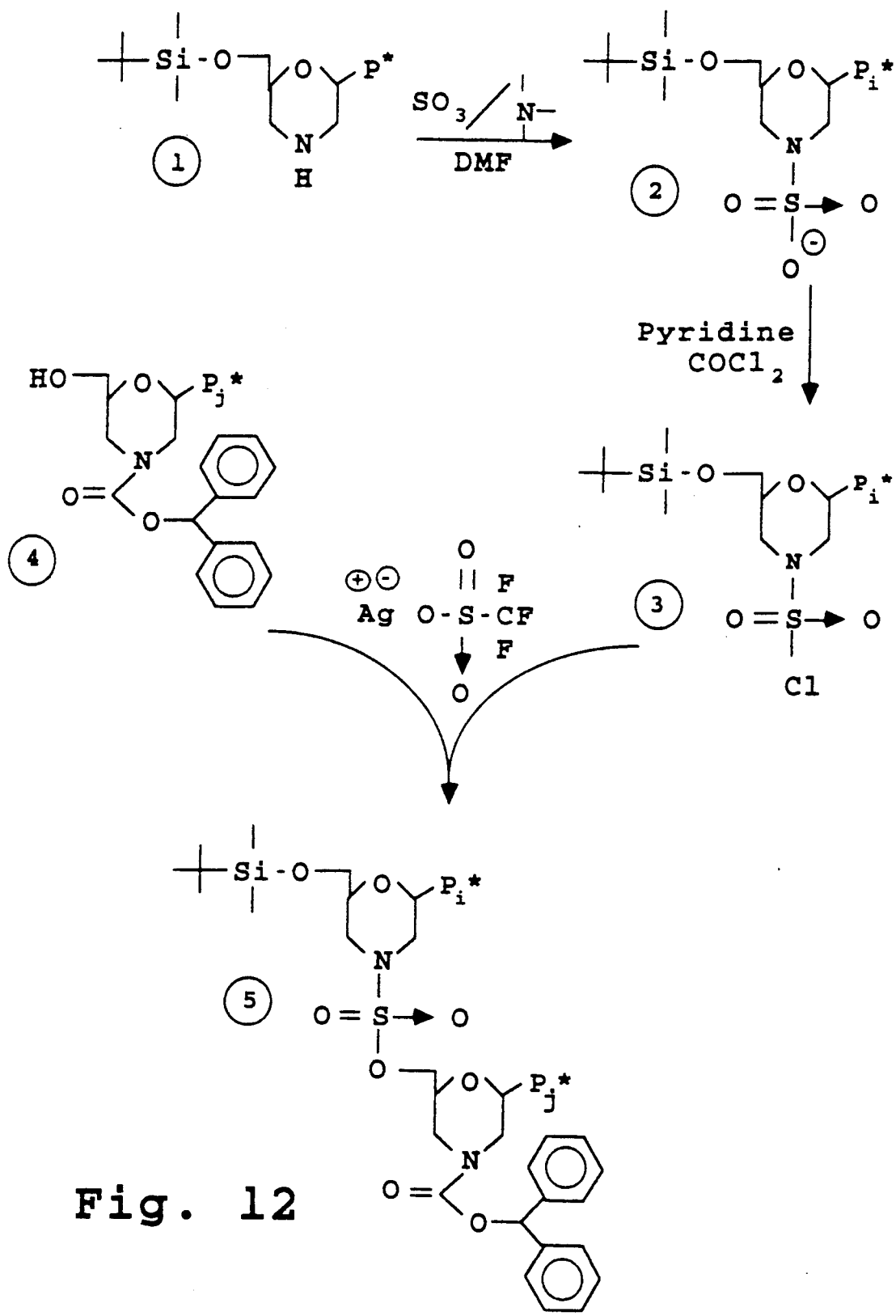
FIG. 12 shows the steps in linking two morpholino subunits through a sulfamate linkage.
Figure 13:
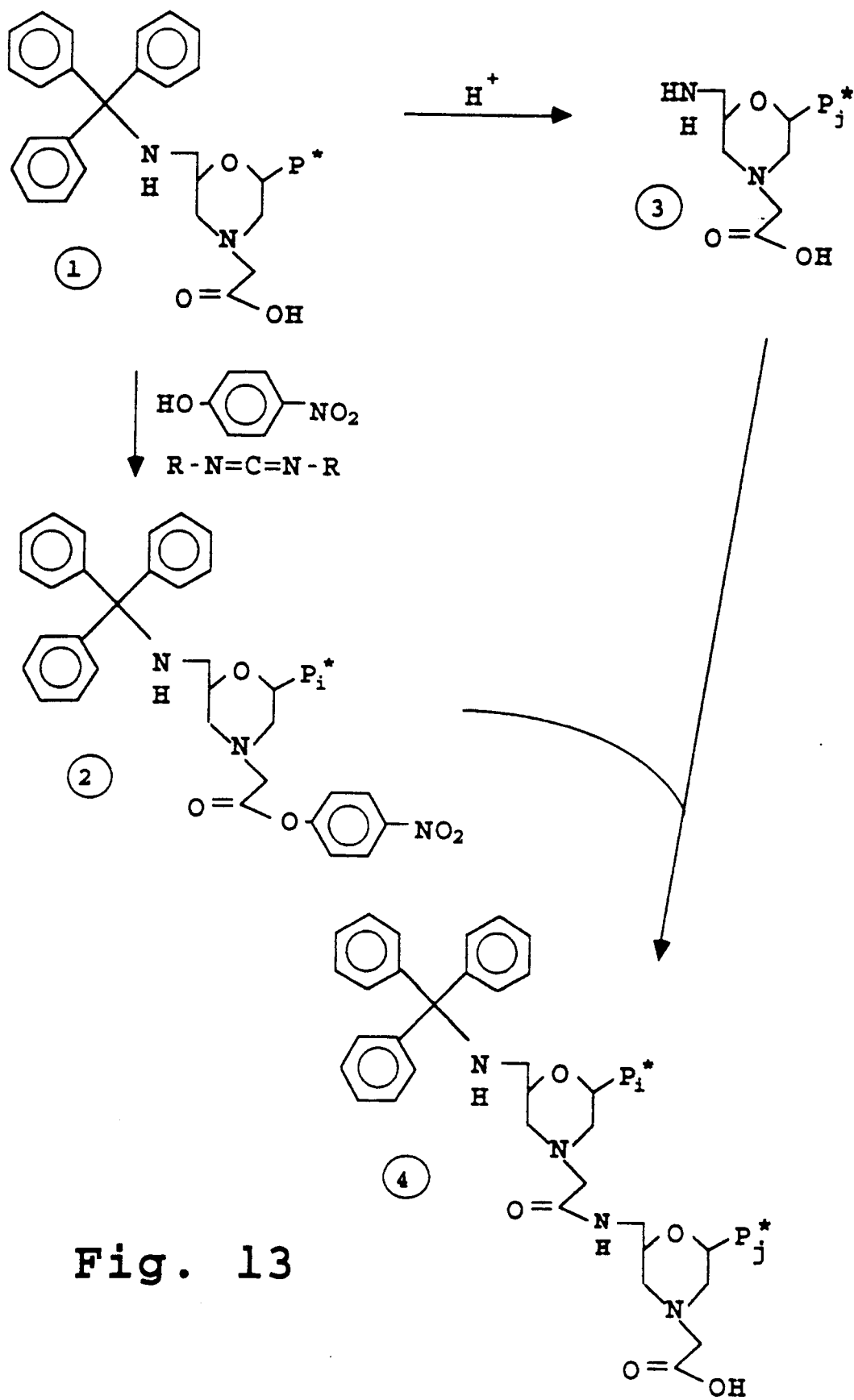
FIG. 13 shows the steps in linking two morpholino subunits through an amide linkage.

Alternatively, the subunits are designed to include a sulfonyl or carbonyl group attached directly or indirectly to the morpholino ring nitrogen, which is coupled to a 5'moiety of a second morpholino subunit (FIGS. 12 and 13). Subunits of this type are suitable for constructing morpholino polymers with 6-atom (FIG. 12) or 7-atom (FIG. 13) repeating-unit backbones.

Figure 7:
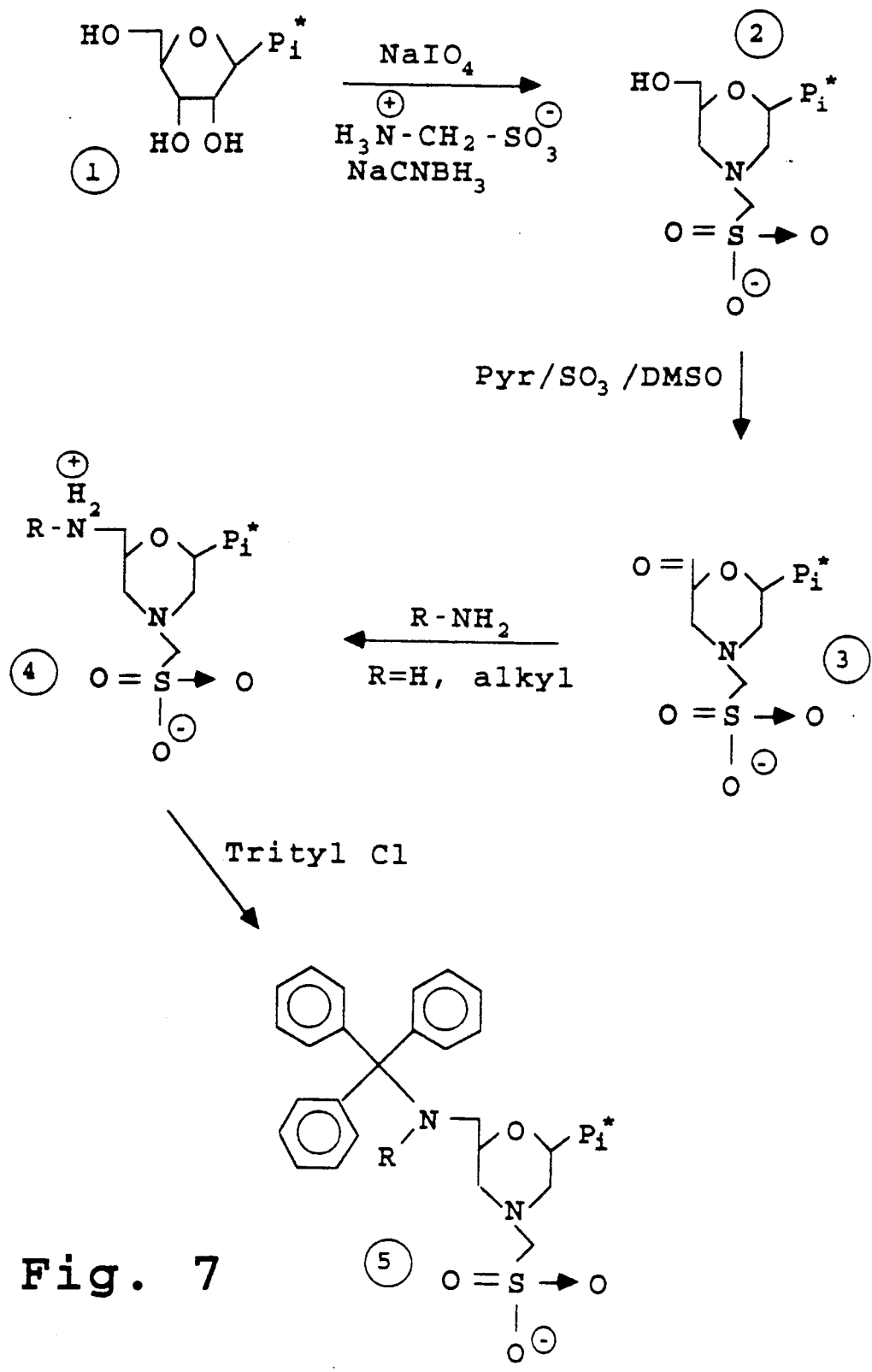
FIG. 7 shows the steps in the synthesis of a morpholino subunit designed for construction of polymers with seven-atom repeating-unit backbones.

An example of the synthesis of a subunit suitable for 7-atom unit-length backbones having an amine at the 5'-carbon atom, and a sulfonyl group linked to the ring nitrogen through a methylene group is detailed in Example 9 (with reference to FIG. 7).

A similar synthesis, described in Example 10, is used to prepare morpholino subunits having a 5'-linked primary amine and an acetyl group linked to the ring nitrogen. This subunit is formed by coupling glycine, rather than AMSA, to the 5' ribonucleoside aldehyde group. Examples 11 and 12 describe, with reference to Structure G of FIG. 3, the preparation of non-morpholino subunits which are converted into morpholino structures during polymer assembly.

C. Activation and Coupling Reactions

The subunits prepared as above are coupled, in a controlled, sequential manner, generally by activating the carbonyl or sulfonyl group on one subunit (having protected nitrogen groups) and contacting this activated subunit with another subunit having an unprotected nitrogen. Different types of linkages, such as those illustrated below, may be employed in the construction of a single polymer.

Figure 9:
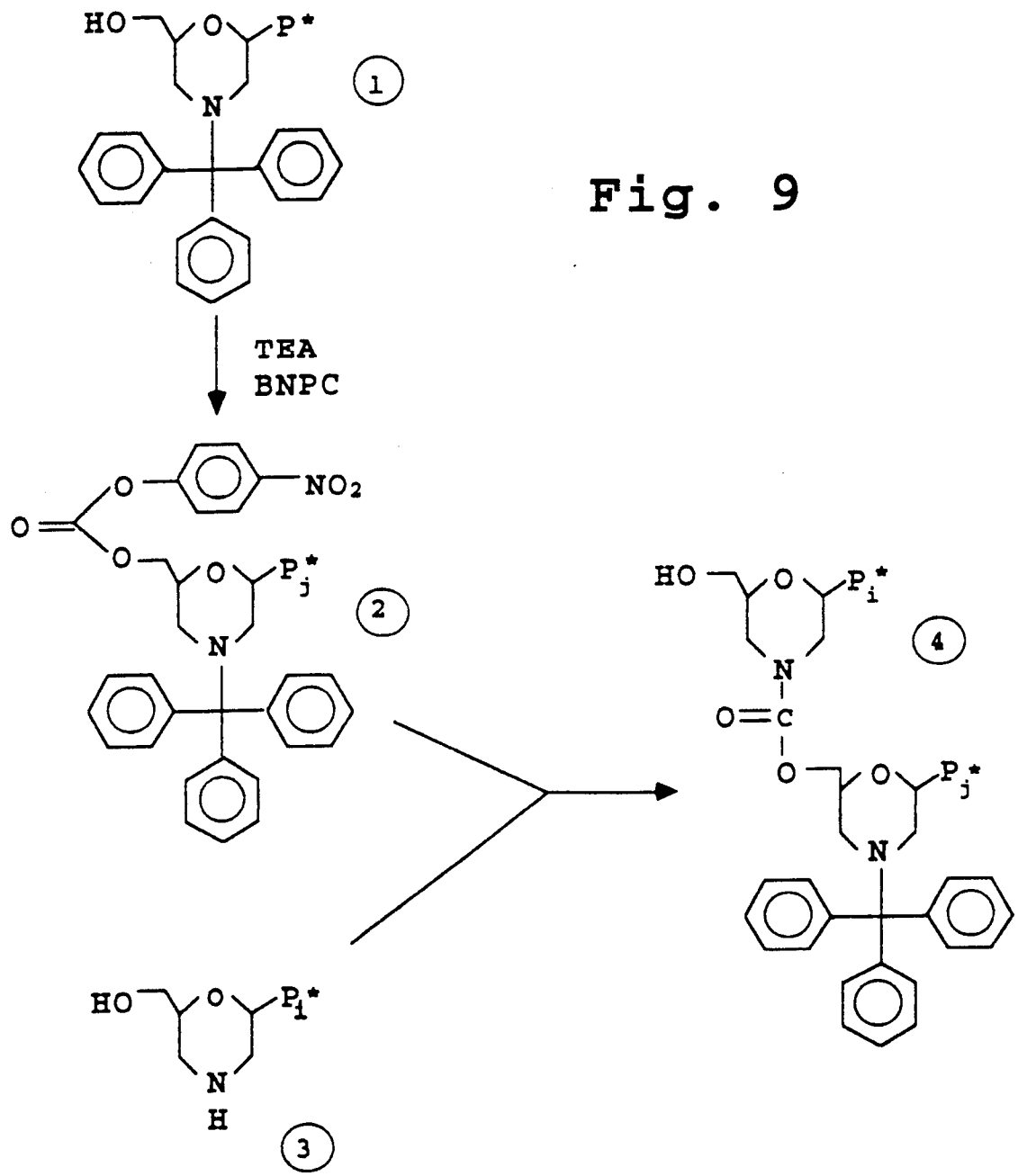
FIG. 9 shows the steps in linking two morpholino subunits through a carbamate linkage.

A number of closely related variations are possible for the carbonyl-containing linkages giving six-atom backbones, corresponding to Structure B—B in FIG. 4. A typical activation and coupling reaction for forming a carbamate linkage (where X is 0 in Structure B—B) is illustrated in FIG. 9. Here a base-protected morpholino subunit with a 5' -OH is reacted with bis-(p-nitrophenyl)carbonate and triethylamine to yield an activated carbonyl subunit (Structure 2, FIG. 9). This activated subunit is then combined with a second base-protected morpholino subunit which may be blocked at the 5' -OH. Bond formation between the subunits occurs between the annular nitrogen on the morpholino ring of subunit 2 and electrophilic carbonyl group of the first subunit, to form a carbamate linkage, where the carbonyl group is C=O. Details of the coupling reaction are given in Example 13.

Activation of the 5' -OH morpholino subunit with p-nitrophenylchlorothioformate and coupling to a second subunit with an unprotected ring nitrogen yields a thiocarbamate linkage (where Y is S in structure B—B of FIG. 4).

The simplest and most obvious morpholino-type binding polymers are the carbamate-linked polymers (type B—B of FIG. 4) where X is oxygen. The polymer has been found to effectively bind to its single-stranded DNA target sequence. However, in binding studies with an RNA target, the polymer exhibited unusual binding, as evidenced by a highly atypical hypochromicity profile in the 320 to 230 nm spectral range and lack of a normal thermal denaturation.

Modeling studies conducted in support of the application indicate that in a carbamate-linked polymer bound to DNA existing in a B conformation the backbone of the polymer provides adequate length for binding and the carbamate moieties of the polymer backbone can assume a nearly planar conformation. This modeling result was in good accord with the effective binding of the carbamate-linked polymers to DNA. In contrast, similar modeling studies suggested that binding of the carbamate-linked polymer to an RNA target requires one of the following: (i) the carbamate linkage of the polymer adopt a substantially nonplanar conformation, or (ii) the RNA target sequence adopt a strained conformation in which base-stacking interactions are quite different from that in a normal A conformation. This observation may explain the atypical binding of a carbamate-linked polymer to an RNA target sequence.

The modeling work further indicated that replacing the carbonyl intersubunit linking moiety with either an achiral sulfonyl-containing intersubunit linkage or with a chiral phosphorous-containing linkage would provide added length of about 0.32 angstrom per intersubunit linkage. This sulfonyl linkage also provides greater rotational freedom about key bonds, and bond angles of the intersubunit linkage compatible with an oligomer backbone conformation suitable for pairing to both RNA and DNA target sequences in their standard conformations. Based on these findings, a number of syntheses of oligomer structures in which morpholino subunits are joined by sulfonyl moieties were subsequently developed and are described below (Structures A—A, C—C, D—D, and E—E of FIG. 4).

Figure 11:
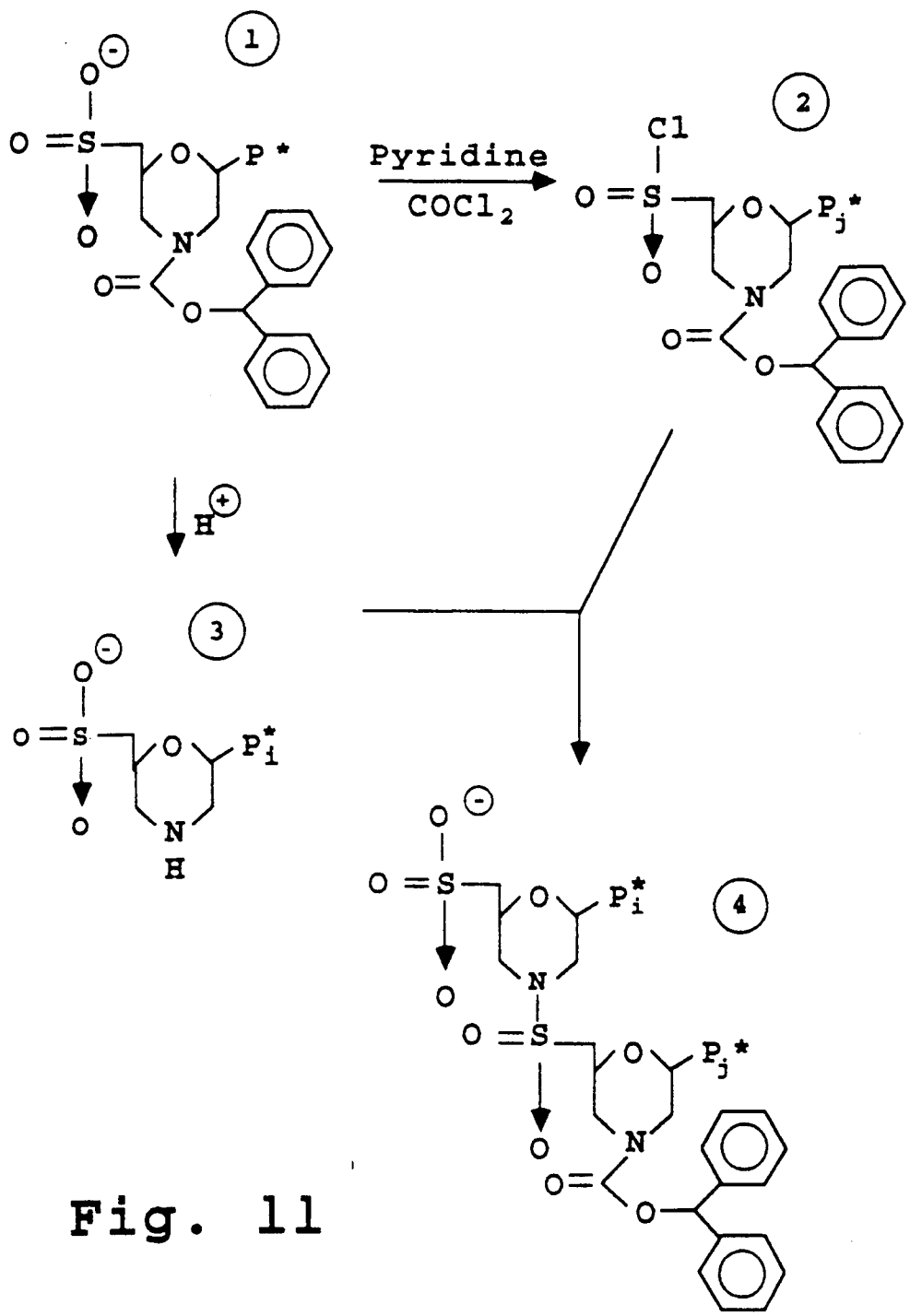
FIG. 11 shows the activation of sulfonic acid and coupling to form a sulfonamide linkage.

The linkage in structure A—A in FIG. 4 (five-atom backbone) can be formed according to the reaction scheme shown in FIG. 11, and detailed in Example 14. Briefly, a 5' -OH morpholino subunit is protected at its ring nitrogen, converted to a 5' SH subunit, then oxidized to convert the 5' -linked sulhydral group to a sulfonyl group. The sulfonyl group is activated with phosgene, and coupled to a second subunit having an unprotected ring nitrogen, as shown. The polymer assembly is continued by deprotecting the morpholino ring nitrogen of the dimer, and reacting the dimer with a third activated subunit.

Figure 10:
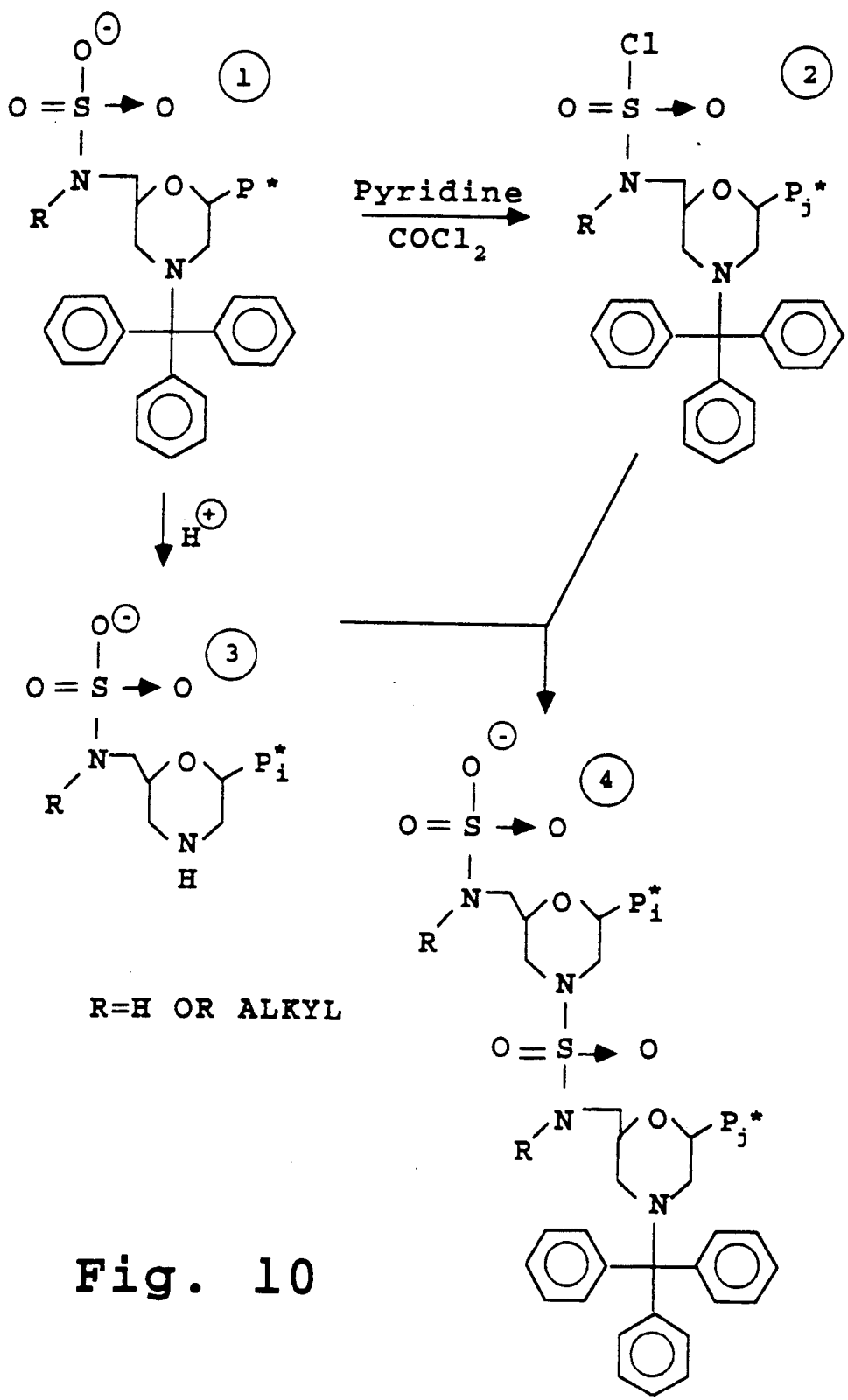
FIG. 10 shows the activation of sulfamic acid and coupling to form a sulfamide linkage.

The sulfamide linkage (corresponding to the linkage in structure C—C in FIG. 4, where X is an amine), is formed by sulfating the 5' -linked amine in a subunit having a protected morpholino ring nitrogen, and then activating with phosgene and reacting this subunit with a second subunit having an unprotected ring nitrogen, as illustrated in FIG. 10. Details of the coupling reaction are given in Example 14.

The sulfamate linkage (corresponding to the linkage in Structure C—C in FIG. 4, wherein X is O) is produced by sulfating the morpholino ring nitrogen of a 5' protected subunit, then using phosgene to generate the sulfamoyl chloride. This activated subunit is then mixed with another subunit or oligomer having a free 5' OH. Coupling of the subunits is achieved either with a catalyst such as silver trifluoromethanesulfonate or use of a strong base to convert the 5' hydroxyl to the anionic form. Conversion of the 5'hydroxyl to the alkoxy can be achieved by KOH and a suitable phase transfer catalyst. This sulfamate coupling is illustrated in FIG. 12 and details are given in Example 15.

A number of 7-atom unit length backbones prepared from the morpholino-subunits (corresponding to structures D—D through F—F in FIG. 4) allow even more flexibility in the construction of polymers which have specified distances between the base-pairing moieties. Using the 7-atom unit length linkages, distances between the morpholino-subunits, and consequently between the base pairing moieties, can be lengthened. Such lengthening of the intersubunit linkage is particularly useful when targeting duplex genetic sequences in a B conformation.

The 7-atom backbone polymers can be readily synthesized from the subunits D-F constructed as above, employing the general coupling reactions described above. For example, Structure D—D in FIG. 4 can be produced by (a) reacting the sulfonyl group of subunit D (FIG. 3) with phosgene, and (b) coupling the activated subunit with a second subunit having an unprotected morpholino ring nitrogen.

Similarly, Structure E—E in FIG. 4 can be produced by activating the sulfonyl group with phosgene, and coupling the activated subunit with a second subunit having an unprotected 5' -linked amine.

Structure F—F in FIG. 4 can be produced by a similar synthetic method in which the carboxyl group is activated with carbonyldiimidazole or a carbodiimide, and the activated compound is reacted with a second subunit having an unprotected 5' -linked primary amine.

Figure 14:
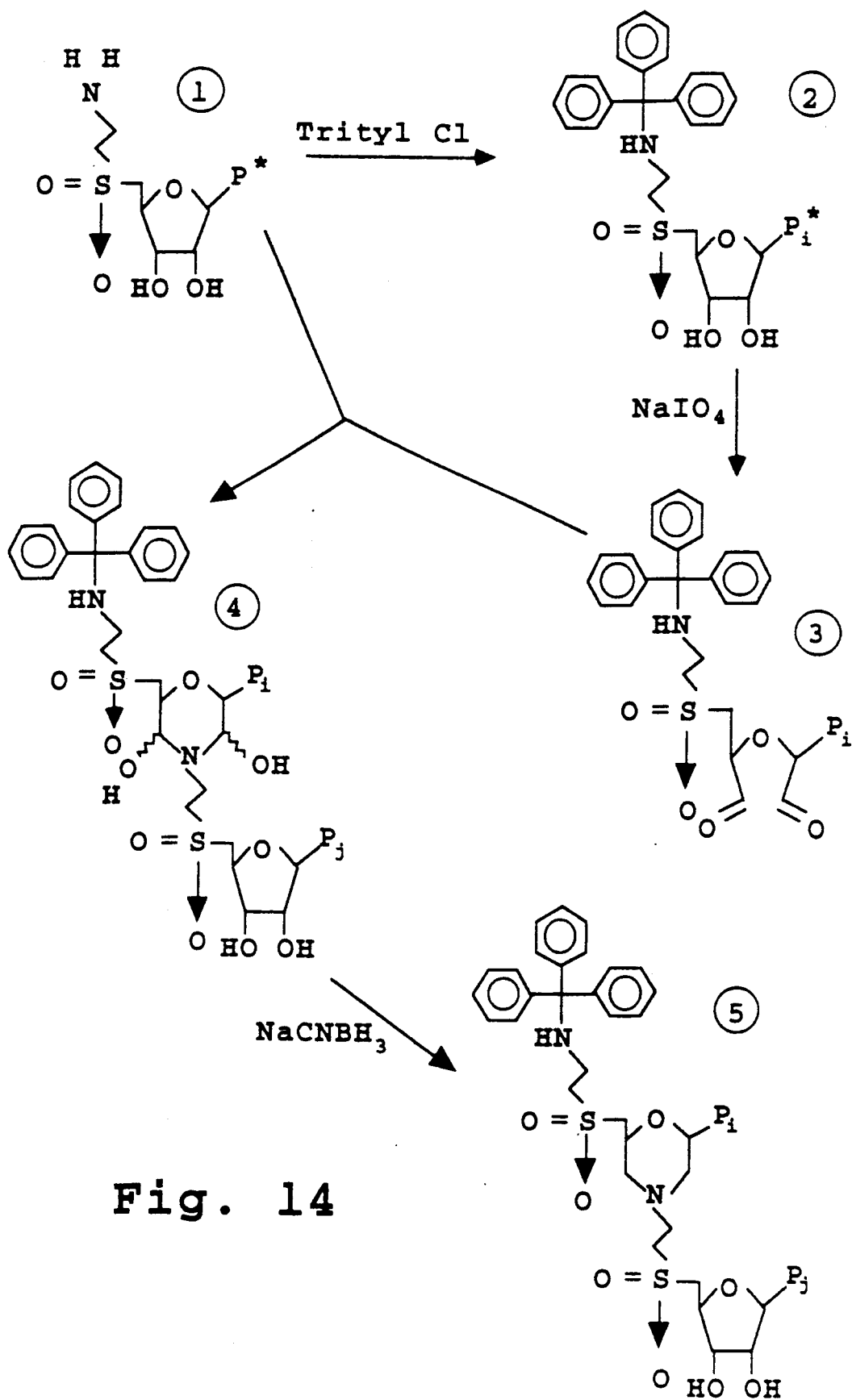
FIG. 14 shows a subunit coupling procedure which simultaneously generates the morpholino ring structure.

A novel class of linkages corresponding to Structure G—G of FIG. 4 can be produced by oxidizing vicinyl hydroxyls of one ribonucleoside subunit and closing the resultant dialdehyde on a primary amine of another subunit followed by reduction with cyanoborohydride. In principle this same scheme could also be used to couple a secondary amine of one subunit and a monoaldehyde of a second subunit; however, the coupling of a ribose-derived dialdehyde to a primary amine proceeds substantially faster and provides a better yield. Examples 11 and 12 describe the synthesis of ribonucleosides containing a primary amine at the 5′. Their use in formation of morpholino polymers is illustrated in FIG. 14.

D. Assembly of Polymers

After selecting a desired polymer length and recognition moiety sequence (guidelines for this are presented below), the polymer is assembled using the general procedures described above. One method of polymer assembly involves initial preparation of an appropriate set of dimers, linking selected dimers to form tetramers, linking these to form octamers, and so on. This method is carried out in solution, substantially according to the coupling methods described with reference to Examples 13-17. Example 18 outlines such a block assembly synthesis using monomers to form dimers, and dimers to form tetramers. The synthesis need not involve oligomers of equal size.

A particular merit of this block assembly method is that each coupling product is roughly twice the length of coupling is simplified. Example 18 details the assembly of a 4-subunit polymer formed by this method.

The polymers may also be synthesized by stepwise subunit addition on a solid support. However, the optimal synthetic approach often uses a combination of the solution and solid support assembly methods where dimers, trimers, or tetramers are synthesized by solution phase and subsequently assembled into the full-length polymer on a solid support, as described in Example 19.

Typically, a solid support, such as glass beads derivatized with acid-stable, long-chain cleavable linkers, are employed as the support material, and prepared for attachment of the first subunit, or block of subunits( as described in Example 19. The glass beads are reacted with a subunit which generally has a readily cleavable protective group on a nitrogen. Whether the morpholino subunit is linked to the support via its morpholino nitrogen or a group at the 5′ position depends on the direction of polymer synthesis, i.e., to which group the next subunit will be attached.

After coupling the second subunit (or oligomer which may be assembled in solution) to the support, any unreacted nucleophilic sites can be capped by addition of a suitable capping reagent, such as p-nitrophenyl acetate or acetic anhydride, and thereafter the support is washed. The protecting group on the nitrogen of the terminal subunit is removed, typically by acid treatment, and after neutralization, the support is reacted with an excess of the next-in-sequence subunit (or polymer unit) which is activated by one of the methods outlined above. One feature of the solid support assembly method is the need for high coupling efficiencies at each subunit addition step. This high coupling efficiency is generally achieved by addition of an excess of the activated subunit which maximizes the number of supportbound chains which are chain-elongated.

Chain elongation is continued in this manner, with optional capping of failure sequences after each subunit addition, until the polymer of the desired length and sequence is achieved.

After addition of the final subunit, the terminal backbone moiety may be reacted with a suitable charged or uncharged group, as described in Example 19. The polymer is then cleaved from the support, e.g., by treatment with either ammonium hydroxide or a nonnucleophilic base suitable for effecting $\beta$-elimination in the linker joining the polymer to the support. The bases are deprotected and the polymer is purified as described below and in Example 19.

E. Polymer Processing and Purification

Binding polymers assembled in solution (Examples 18 and 20) are typically base-deprotected by suspending in DMSO or DMF and layering on the suspension an equal volume of concentrated ammonium hydroxide. The preparation is mixed with shaking and incubated at 30° C. for 16 hrs. Workup includes removing the ammonia under reduced pressure. If a protective group (generally trityl or a related acid-labile moiety) is present, this group is cleaved and the crude polymer preparation is suspended in the appropriate buffer for purification (Example 19).

Binding polymers assembled by a solid-phase method (Example 19) wherein they are linked to the support via an ester linkage can be cleaved from the support by suspending the dried support in DMSO, layering on an equal volume of concentrated $NH_4OH$, capping tightly, and slowly agitating for 16 hrs at 30° C. The solid support material is removed by filtration and the filtrate is treated as described above.

Alternatively, binding polymers linked to the support via a $\beta$-elimination-sensitive linker can be cleaved from the support using a strong non-nucleophilic base 1,8 diazabicyclo (5.4.0.)undec-7-ene (DBU) in DMF. Using this approach one can release the polymer with its bases still protected and thus the polymer is suitable for further modification and/or structural confirmation via fast atom bombardment mass spectroscopy.

Purification of the base-deprotected polymer is preferably carried out at pH 2.5 or pH 11, depending on the pKs of the base moieties in the polymer. At pH 2.5 cytosine, adenine, and 2-6-diaminopurine moieties carry a positive charge and guanine carries a partial positive charge. At pH 11 guanine, uracil and hypoxanthine carry a negative charge.

For polymers in which about 50% or more of the base-pairing moieties are ionized at pH 2.5, the purification can be carried out by cation exchange on a column of S-Sepharose fast-flow (Pharmacia) developed with a shallow NaCl gradient buffered at pH 2.5. The effluent is monitored at 254 nm and collected in a fraction collector. The full length polymer, which elutes after the shorter failure sequences, can be further purified and desalted on a column of chromatographic grade polypropylene (Polysciences Inc.), eluted with an aqueous gradient of acetonitrile adjusted to pH 2.5 with formic acid, with the eluant being monitored at 254 nm. The fractions containing the pure product are neutralized and dried under reduced pressure. Salts may be discarded by dissolving the polymer in trifluoroethanol, filtering, and evaporating the trifluoroethanol.

For polymers in which about 50% or more of the basepairing moieties are ionized at pH 11, the purification may be performed on an anion exchange column of Q Sepharose fast-flow (Pharmacia) developed with an aqueous pH 11 gradient of NaCl. The full-length polymer, which elutes after shorter failure sequences, is further purified and desalted on a polypropylene column eluted with an aqueous pH 11 gradient of acetonitrile. Fractions containing the pure product are processed as above.

The purification methods described above should be carried out so that polymers containing adenine base-pairing moieties are not exposed to pH 11 for more than a few hours at room temperature, to avoid potential base lability problems. The details of the purification methods are outlined in Example 19.

In neutral, aqueous solution, longer morpholino polymers may have solubilities only in the sub-micromolar range. Therefore, it may be advantageous to enhance polymer solubility by addition of one or more hydrophilic moieties, e.g., polyethylene glycol. For most of the polymer types disclosed herein, this can be accomplished by cleaving the terminal backbone protective group from the completed polymer, and reacting the polymer, with the bases still in the protected state, with excess of carbonyldiimidazole-activated polyethylene glycol (PEG). Thereafter the binding polymer is treated with ammonium hydroxide to remove the base-protected groups, and the polymer is purified as above. The level of solubilization is easily adjusted through proper selection of the PEG material. Suitable PEG fractions having average molecular weights of 200, 400, 600, 1,000, 1,540, 3,400, 4,000, 6,000, 7,500, and 18,500 daltons are commercially available (e.g., Polysciences, Inc.) with PEG1000 often providing the best solubilization. The solubilizing moiety may be linked to the polymer through a cleavable linkage, if desired, to allow the polymer to be released from the solubilizing agent, e.g., by esterase or peptidase enzymes.

It will be appreciated that the polymer may be further derivatized or labeled according to known procedures. For example, the polymer may be radiolabeled by preparing the polymer subunits from radiolabeled ribonucleosides or by attaching a radiolabeled amino acid at one terminus. The polymer may be readily derivatized, e.g., employing modifications of the above subunit coupling reactions, with enzymes, chromophoric groups, or the like, where the polymer is to be used as a diagnostic probe. Further, the polymer may be derivatized with biomolecules which serve to target the polymers to specific tissues or cell types.

F. Structural Characterization

Fully-protected binding polymers of moderate size (10 to 20 subunits) often give a strong molecular ion in FAB (Fast Atom Bombardment) mass spectroscopy, providing a key confirmation of the polymer length.

Further, COSY-NMR (two-dimensional correlated spectroscopy) of the deprotected and purified polymer provides information on the ratio of the different base-pairing moieties in the polymer as well as quantitative information on the ratio of binding polymer to any solubilizing or other type moiety which may have been linked thereto.

Mobilities on ion exchange columns also provide information on the number of C +A base-pairing moieties in a polymer when purification is carried out at ph 2.5 and information on the number of G +U residues when the purification is run at pH 11. Structural verification is easiest when the polymers have been assembled from oligomer blocks, such as in Examples 18, 19 and 20, since any failure sequences then differ more substantially from the full-length sequences.

The UV profiles of the polymers at pH 1, 7, and 13 can provide information about the relative nucleotide composition of the polymer.

Assessment of a morpholino-based polymer's affinity for its target sequence is carried out by examining the melting curve of the polymer/target duplex, as illustrated in Examples 20 and 21.

Further, comparisons can be made between the melting curve of a regular nucleic acid duplex (such as $p(dC)_4/p(dG)_6$) and the melting curve of a hybrid duplex containing a corresponding morpholino-based polymer (such as (morpholino-based C)$_4$/p(dG)$_6$). Characterization of the synthetic intermediates and the full-length oligomer was achieved by proton NMR and negative ion FAB mass spectroscopy. With these carbamates of the morpholino oligomers, the fragmentation of the oligomers is greatly suppressed so that little sequence information is available. However, the parent ion signal is quite strong and allows confirmation of the composition of the morpholino oligomer (see Example 20). High resolution mass spectrometry of the morpholino-based poly C hexamer provided a satisfactory elemental analysis.

Several features of the proton spectrum of the oligomers were of interest. For example, the length of the oligomers could be ascertained by comparing the integration of the various signals. For example, in a dimer the two 2' protons were separated by 0.5 ppm and gave a 1.02/1 ratio of integrations and for the hexamer, this ratio was 4.65/1 against the expected value of 5/1.

The bases of the above hexamer were deprotected by treatment with concentrated ammonia for 24 hours. The 4'-terminal morpholino ring nitrogen was liberated by treatment of the crude oligomer with 1% formic acid in trifluoroethanol. In order to assess the stability of these molecules under these conditions, a precursor dimer was treated with concentrated ammonia for 60 hours; no cleavage of the intersubunit linkage was observed. Under all conditions used to date, no cleavage of the carbamate linkage under acidic conditions has occurred.

The hexamer was taken up in pH 2.5 buffer and purified by cation exchange chromatography on S-Sepharose Fast Flow ™, eluting with potassium chloride gradients. The chromatograms showed one major peak comprising over 95% of the cytosine-containing materials in the mixture, and confirming that little or no cleavage of the oligomer occurs in the deprotection of the bases and the morpholino-amine. After neutralization the hexamer was desalted on a polypropylene column eluted with a water-acetonitrile gradient.

The purified hexamer was analyzed by $^1$H NMR. The assignment for the protons was made on the basis of a COSY plot. One cytosine base has signals that were found downfield relative to the other bases (8.04 to 7.65 and 6.78 to 5.85 ppm). The relative integrations of these peaks confirmed that the hexamer was deprotected and has been purified intact. The 5' protons were assigned to the signal at 4.35–4.15 downfield of the 1' proton signal at 4.14–3.90 ppm. These chemical shifts run against the trend identified in the protected oligomers where the 1' proton of the same base(s) was always downfield of the 5' protons of the same base(s). Apparently the benzoyl groups in the protected oligomers play a role in shaping the environment of the ' and 5' protons.

The solubility of the hexamer was found to be 4 μM in pH 7.5 buffer. In order to increase water solubility of the hexamer a polyethylene glycol (PEG) tail was attached to the oligomers. 5 equivalents of PEG 1000 was treated with one equivalent of bis(p-nitrophenyl)carbonate to give monoactivated PEG. Detritylation of the hexamer with 1% formic acid in trifluoroethanol afforded a free amine. Treatment of the hexamer containing the free amine with activated PEG1000 under standard coupling conditions resulted in attachment of the PEG tail to the hexamer. The bases were deprotected by treatment of the tailed hexamer with concentrated ammonia for 24 hours. The tailed hexamer was taken up in pH 2.5 buffer and purified by cation exchange chromatography on S-Sepharose Fast Flow TM eluted with a potassium chloride gradient. After neutralization the eluant was desalted on a polypropylene column eluted with a water/acetonitrile gradient. The tailed hexamer was found to be freely soluble in pH 7.5 buffer in concentrations up to 2 mM.

The characterization of the tailed hexamer by the $^1$H NMR methods employed above was not possible. In the spectrum of the tailed hexamer there was no differentiation between the signals of the base protons, thus precluding the assessment of the oligomer length. Additionally, the envelope containing the PEG tail signals obscured the majority of the signals of the morpholino rings. However, the ion exchange chromatography of the tailed hexamer gave one major peak indicating little or no cleavage of the oligomer during deprotection. The pattern of the chromatogram of the tailed hexamer was the same as found for the free hexamer, except that the tailed hexamer elutes faster than the free hexamer.

The stability of complexes of the tailed hexamer with complementary nucleic acids was investigated by thermal denaturation experiments. Difference spectra between mixed and unmixed samples of the tailed hexamer and the selected phosphodiester complement were obtained from 14° C. to 85° C. and over the 320 to 260 nm range (see Example 20). As a control, the duplex of p)dC)$_6$ with p(dG)$_6$ was thermally denatured. The difference UV spectrum of the tailed hexamer (morphC)$_6$ with p(dG)$_6$ was similar to that of the control DNA duplex, p(dC)$_6$ with p(dG)$_6$, except that the amount of hypochromicity before denaturation of the (morphC)$_6$/p(dG)$_6$ duplex was much greater than that of the control. The thermal denaturation of the p(morphC)$_6$/p(dG$_6$) duplex gave a $T_m$ value of 62.5° C. (see Example 20 and FIG. 15). The corresponding DNA/DNA duplex gave a Tm value of 26.5° C.

G. Diagnostic Applications

The target-specific polymers of the invention can be used in a variety of diagnostic assays for detection of RNA or DNA having a given target sequence. In one general application, the polymers are labeled with a suitable radiolabel or other detectable reporter group. Target polynucleotide, typically a single stranded polynucleotide which is bound to a solid support, is reacted with the polymer under hybridization conditions, allowed to anneal, and then the sample is examined for the presence of polymer reporter group.

The diagnostic assay can be carried out according to standard procedures, with suitable adjustment of the hybridization conditions to allow polymer hybridization with the target region. In this regard, it is noted that the polymer can be designed for hybridization with the target at a higher melting temperature than the complementary polynucleotide strand, since polymer binding does not entail backbone charge repulsion effects. Therefore, the polymer can bind to the target at a temperature above the normal polynucleotide melting temperature, an important advantage of the polymer over conventional oligonucleotide probes. This binding at elevated temperature minimizes the problem of competition for binding to the target between the probe and any corresponding single-strand oligonucleotide which may be present in the diagnostic mixture.

In a second general type of diagnostic application, the polymers are linked to a solid support, for capture of target RNA or DNA to the support. The solid support, e.g., polymeric microparticles, can be prepared by linking the polymers to the support according to the methods described above or by conventional derivatization procedures. Alternatively, where the polymers are synthesized on a solid support this support may also serve as the assay support.

According to an important feature of this assay system, the target polynucleotide molecules which are captured on the support by base-specific binding to the polymers can be detected on the basis of their backbone charge, since the support-bound polymers are themselves substantially uncharged. To this end, the assay system may also include polycationic reporter molecules which are designed to bind to the fully charged analyte backbone, but not the uncharged (or substantially uncharged) polymer backbone, under selected binding conditions.

In one embodiment the reporter molecules are composed of a polycationic moiety or tail designed to bind electrostatically to a fully charged polynucleotide, under conditions where the reporter does not bind to the less charged or uncharged binding polymer carried on the diagnostic reagent; one or more reporter groups may be attached to the tail, adapted to produce a signal by which the presence of the reporter can be detected. Methods for forming polycationic molecules and for attaching reporter molecules to cationic compounds are known in the art.

Each reporter molecule carries one or more reporter groups, and each polynucleotide can accommodate binding of typically several thousand or more reporter molecules. Thus the system has an amplification factor, in terms of reporter signal per bound analyte molecule, of several orders of magnitude. In addition, the method has the advantage, noted above, that the polynucleotide binding reaction can be carried out under conditions in which binding competition with complementary nucleotide strands does not occur.

The design considerations applied in preparing a polynucleotide binding polymer for use as a diagnostic reagent are governed by the nature of the target analyte and the reaction conditions under which the analyte is to be assayed. As a first consideration, there is selected a non-homopolymeric target base sequence against which the polymer is directed. This target sequence is generally single-stranded and preferably unique to the analyte being assayed.

The probability of occurrence of a given n-base target sequence is approximately $(\frac{1}{4})^n$. Accordingly, a given n-base target sequence would be expected to occur approximately once in a polymer containing $4^n$ bases. Therefore, the probability P that a given n-base sequence will occur in polynucleotides containing a total of N unique-sequence bases is approximately $P=N/4^n$. To illustrate, the probability P that a 9-base target sequence will be found in a 20 kilobase polynucleotide is about $20 \times 10^3/2 \times 10^5$ or 0.08, the probability that a 16-base target sequence will be present is about $20 \times 10^3/4.3 \times 10^9$ or 0.0000047. From these calculations, it can be seen that a polymer having 9–16 recognition moieties specific for a defined 9–16 base target sequence should have high specificity for the target sequence in an assay mixture containing only viral genomes, whose greatest complexities correspond to about 400K of unique-sequence bases.

Similar calculations show that a 12 to 16 subunit polymer can provide adequate specificity for a viral or bacterial target sequence in an assay mixture containing viral and bacterial genomic material only; largest genomic sizes about 5,000 kilobases. A 16 to 22 subunit polymer can provide adequate specificity for a target sequence in a polynucleotide mixture containing mammalian genomic DNA material; genomic sizes of about 5 billion base pairs of unique-sequence DNA.

The polymer/analyte binding affinity, and particularly the temperature at which the polymer just binds with the target sequence (the melting temperature, or Tm) can be selectively varied according to the following criteria: (a) number of subunits in the polymer; (b) the number of hydrogen bonds that can be formed between the base-pairing moieties and the corresponding, complementary bases of the analyte target sequence; (c) unit length of the polymer back concentration of denaturants, such as formamide, which reduces the temperature of melting.

From a number of studies on model nucleic acid duplexes it is known that the melting temperature of oligonucleotide duplexes in the 10 to 20 bp range increases roughly 3° C. per additional base pair formed by two hydrogen bonds, and about 6° C. per additional base pair formed by three hydrogen bonds. Therefore, the target sequence length originally selected to insure high binding specificity with the polymer may be extended to achieve a desired melting temperature under selected assay conditions.

Also, where the recognition moieties used in constructing the polymer are the standard nucleic acid bases the target sequence may be selected to have a high percentage of guanine plus cytosine bases to achieve a relatively high polymer/analyte melting temperature. On the other hand to achieve a lower melting temperature a target sequence is selected which contains a relatively high percentage of adenine plus thymine bases.

Figure 16:
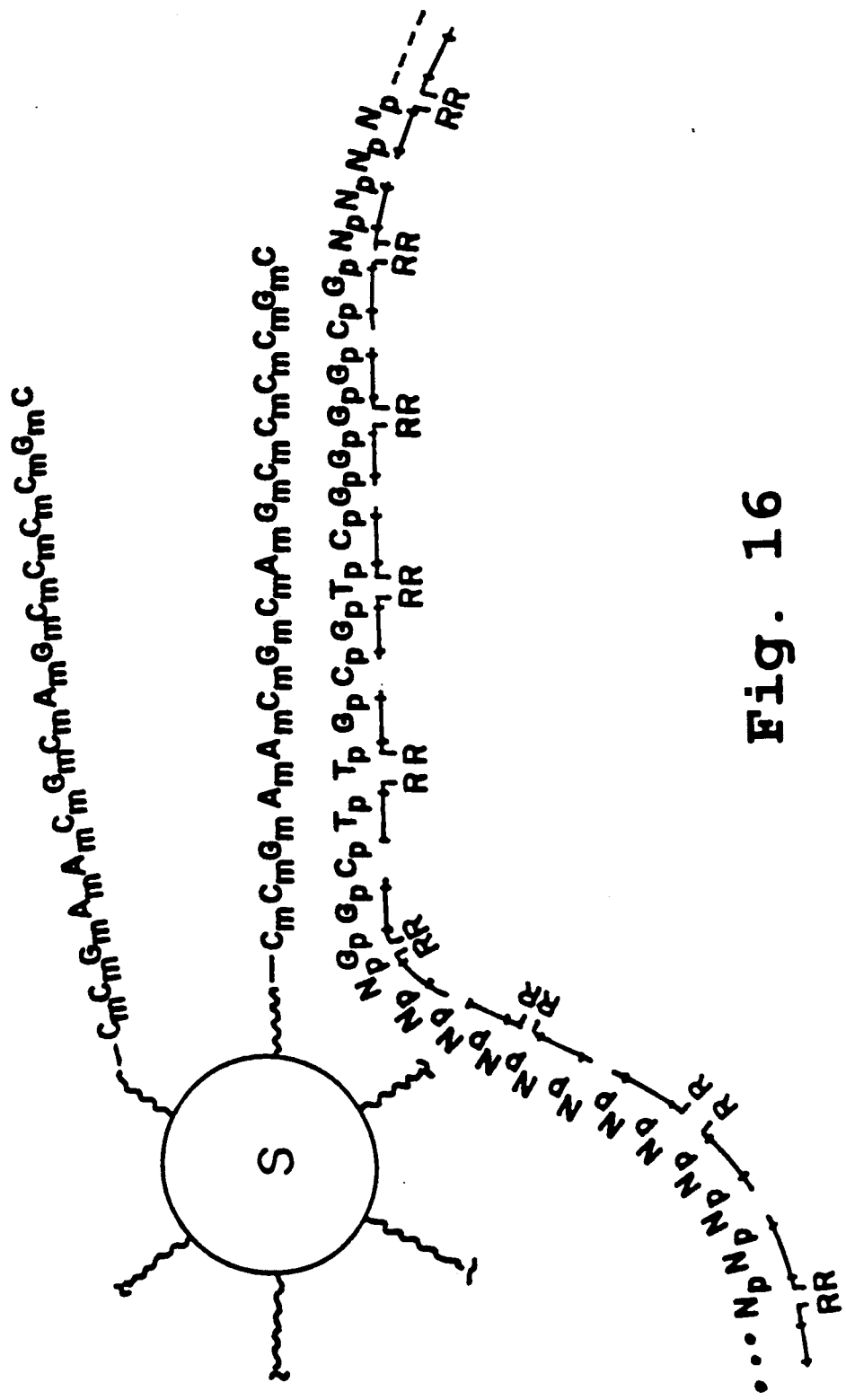
FIG. 16 illustrates a diagnostic solid-support particle employing polymers of the present invention for use in a probe-diagnostic assay.

The binding components in the diagnostic system, as they function in the solid-support diagnostic method just described, are illustrated in FIG. 16. Here "S", the assay reagent, is the solid support having a number of binding polymers attached to its surface through spacer arms indicated by sawtooth lines. In the assay procedure, the target DNA in single strand form is reacted with the support-bound polymers under hybridization conditions, and the solid support is then washed to remove non-hybridized nucleic acid material.

The washed support is then reacted with the reporter, under conditions which favor electrostatic binding of the reporter cationic moiety to the target DNA backbone. The reporter shown in FIG. 16 is a dicationic molecule having a reporter group R.

After reaction with the reporter solution, typically at room temperature for 1–2 minutes, the reagent is washed to remove unbound reporter, and then the assay reagent is assessed for bound reporter. One approach in determining the amount of reporter associated with the reagent, particularly in the case of fluorescent or chromophoric reporter groups, is to elute the reporter from the reagent with a high salt solution and then assess the eluate for reporter.

Figures 8A, 8B:
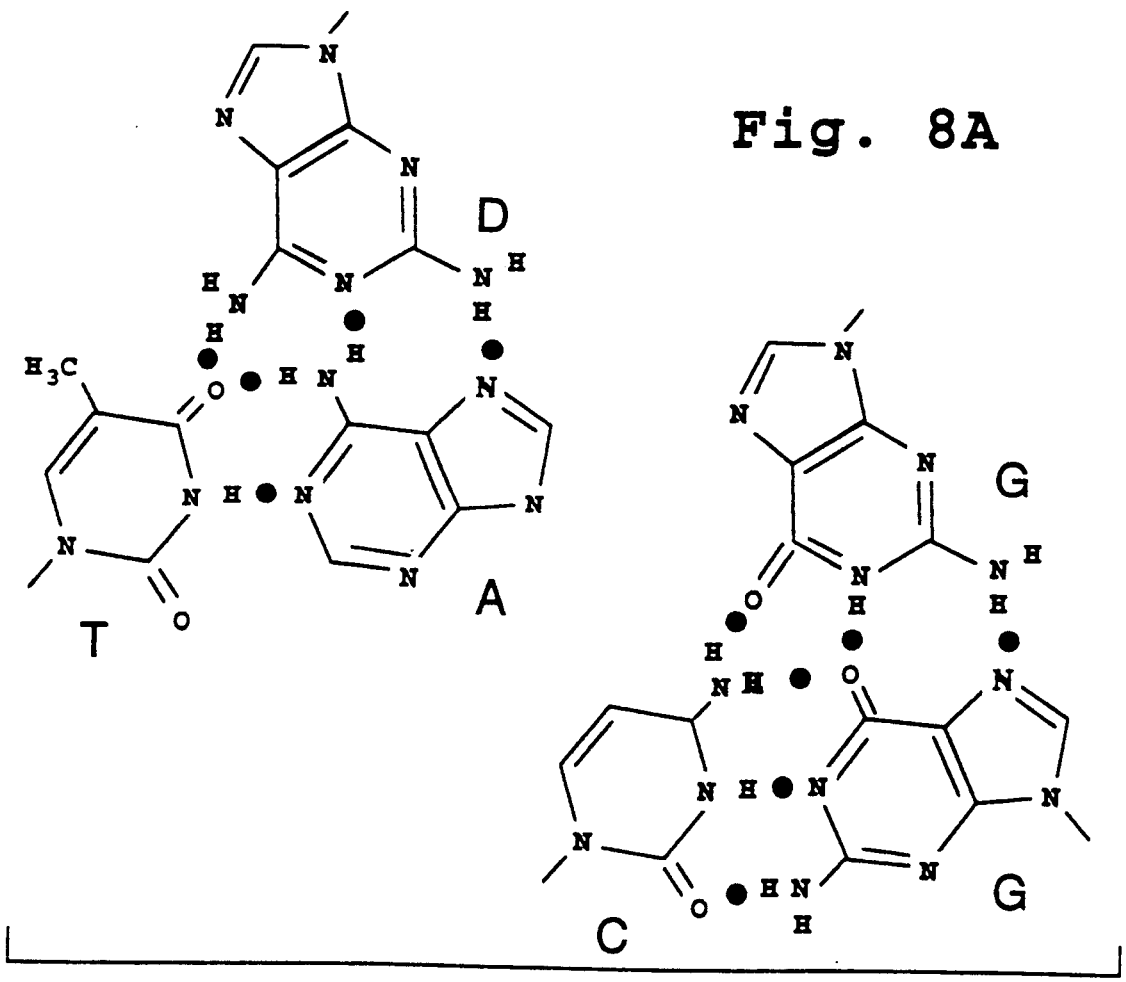
In FIG. 8b, a = Adenine; c = cytosine; g = guanine; t = thymine; u = uracil; D = 2,6-Diaminopurine or 2-aminopurine; G = Guanine or thioguanine; | = high specificity hydrogen bonding; and : = low specificity hydrogen bonding.

The polymer of the invention can undergo sequence-specific binding to duplex nucleic acids via base-pair-specific hydrogen bonding sites which are accessible through the major groove of the double helix. This bonding can occur in a duplex region in which at least 70% of the bases on one strand are purines and a corresponding percent of the bases on the other strand are pyrimidines. The duplex binding polymer preferably includes 2-aminopurine or 2,6-diaminopurine hydrogen bonding moieties for binding to T-A or U-A base pairs, and guanine or thioguanine hydrogen-bonding moieties for binding to C-G base pairs as illustrated in FIG. 8A. Thus, for these special target sequences (an example of which is shown in FIG. 8B), the polymer of the invention can be used for diagnostic assays of the types just described, but where the target nucleic acid is in non-denatured, duplex form.

H. Other Applications

The polymers of the instant invention can be used in place of standard RNA or DNA oligomers for a number of standard laboratory procedures. As mentioned above, morpholino-based polymers can be fixed to a solid support and used to isolate complementary nucleic acid sequences, for example, purification of a specific mRNA from a poly-A fraction (Goldberg et al). The instant polymers are advantageous for such applications since they are inexpensive and straightforward to prepare from activated subunits.

A large number of applications in molecular biology can be found for labeled morpholino-based polymers. Morpholino-based polymers can be easily and efficiently end-labelled by the inclusion in the last step of the polymer synthesis an activated and labelled morpholino-based subunit or, preferably, an $^{35}$S-labelled methionine. The type of label to be used is dependent on the final application of the polymer, and includes radioactive ($^3$H, $^{14}$C, $^{32}$P, or $^{35}$S) nucleosides and biotin. Labelled morpholino-based oligonucleotide analogs can act as efficient probes in, for example, colony hybridization (Grunstein et al), RNA hybridizations (Thomas), DNA hybridizations (Southern), and gene bank screening (Szostak et al).

The polymers of the invention also have important potential use as therapeutic agents. Recently, uncharged anti-sense nucleic acid analogs, which are nearly isostructural with DNA, have been used as antiviral and anti-tumor agents. The polymers of the present invention provide several advantages over the more conventional anti-sense agents.

First, the morpholino polymers are substantially less expensive to synthesize than oligonucleotides. This is due in part to the fact that the morpholino subunits used in polymer synthesis are derived from ribonucleosides, rather than the much more expensive deoxyribonucleosides. Also, as noted above, the coupling reaction between a phosphorous and an amine of a second subunit occurs under relatively mild conditions, so that protection steps and other precautions needed to avoid unwanted reactions are simplified. This is in contrast to standard ribo- and deoxyribonucleotide polymer synthesis where coupling through a phosphate ester linkage requires that the coupling reagents be highly reactive and that the reaction be carried out under stringent reaction/protection conditions. This advantage in polymer synthesis also applies, of course, to diagnostic uses of the polymer.

Second, polymer binding to its target may give substantially better target inactivation, since the polymer/target duplex is not susceptible to duplex unwinding mechanisms in the cell.

Third, the morpholino-based polymer is also more stable within the cell; the polymer backbone linkage is not susceptible to degradation by cellular nucleases.

Fourth, in therapeutic applications involving cellular uptake of the compound, the uncharged morpholino polymer is more likely to efficiently enter cells than a charged oligonucleotide.

In the context of therapeutic applications, the morpholino polymers of the present invention may be targeted against double-stranded genetic sequences in which one strand contains predominantly purines and the other strand contains predominantly pyrimidines (e.g., FIG. 8B).

Further, when a messenger RNA is coded by the mostly purine strand of the duplex target sequence, morpholino binding polymers targeted to the duplex have potential for also inactivating the mRNA. Thus such a polymer has the potential for inactivating key genetic sequences of a pathogen in both single-stranded and double-stranded forms.

In 1981 it was reported that short (3 to 7 subunits) methylphosphonate-linked DNA analogs complementary to portions of the Shine-Dalgarano consensus sequence of procaryotic mRNAs were effective in disrupting bacterial protein synthesis in bacterial lysates and in a special permeable strain of bacteria. However, such agents failed to inhibit protein synthesis in normal bacteria (Jayaramon, 1981).

Experiments performed in support of the instant invention show that polymers of 3 to 5 subunits in length can be effective to block protein synthesis in normal bacteria by using a combination of bases which result in a high target-binding affinity. More specifically, the following oligomers and oligomer combinations can perturb protein synthesis in normal intact bacteria (where D is 2,6-Diaminopurine or adenine; G is Guanine; B is 5-Bromouracil, other 5-Halouracil or uracil; sequences are shown with their 5' end to the left): DGG, BDDG, DDGG; DGGD; GGDG; GDGG; DGGB; GGBG; GGAGG; GGDGG; and the combinations BDD +GGDG; DDG +GDGG; DGG +DGGB; GGD +GGBG; BDDG +GDG; DDGG +DGG; DGGD +GGB GGDG +GBG; BDD +GGDG +GBG.

While other backbone types may be suitable for such binding-enhanced short oligomers (e.g., carbamate-linked deoxyribonucleosides; Stirchak, 1987), the morpholino type oligomers of the present invention are preferred on the basis of starting material costs and ease of assembly.

The use of short binding-enhanced oligomers to disrupt the biological activity of an RNA sequence which plays a key role in the metabolism of a target class of organisms but not a correspondingly important role in higher organisms should be broadly adaptable to a variety of pathogenic organisms (e.g., bacteria and fungi) having a cell wall which excludes the entrance of longer polymers.

The following examples illustrate methods of subunit and polymer synthesis, and uses of the polymer composition of the invention. The examples are in no way intended to limit the scope of the invention.

EXAMPLE 1

Base Protection of Ribonucleosides

The following ribonucleosides are obtained from Sigma Chemical Co. (St. Louis, MO): uridine, guanosine, 5-methyluridine, adenosine, cytidine, 5-bromouridine, and inosine.

2,6-diamino-9-(B-D-ribofuranosyl)-9H-purine (2,6-diaminopurine riboside) is obtained from Pfaltz and Bauer, Inc., Division of Aceto Chemical Co., Inc. (Waterbury, CT).

The following nucleosides are prepared by the literature methods indicated:

1-$\beta$-D-ribofuranosyl)-2-pyrimidinone (2-hydroxypyrimidine riboside) is prepared by the procedure of Niedballa.

2-amino-9-$\beta$-D-ribofuranosyl)-1,6-dihydro-6hpurine-6-thione (thioguanosine) is prepared by the procedure of Fox.

Dimethoxytrityl chloride, N-6-benzoyladenosine, N-4-benzoylcytidine, and N-2-benzoylguanosine are obtained from Sigma Chemicals. 9-fluorenylmethoxycarbonyl chloride (FMOC chloride), trimethylchlorosilane, isobutyric anhydride, 4-nitrobenzoyl chloride, naphthalic anhydride, and all organic solvents for reactions and chromatography were obtained from Aldrich Chemical Co. (Milwaukee, WI). Silica Gel is obtained from EM Science (Cherry Hill, NJ).

When activation of the subunits is achieved using dihalogenated electrophiles (eg. $COCl_2$, or $SO_2ClF$), better yields of activated subunits are often obtained by using protective groups which leave no acidic protons on the purine and pyrimidine exocyclic amines. Examples of such exocyclic amine moieties are as follows: the $N_6$ of adenine, the $N_4$ of cytosine, the $N_2$ of guanine, and the $N_2$ and $N_6$ of diaminopurine. Suitable protective groups for this purpose include the naphthaloyl group (Dickshit) and the amidine groups developed by McBride et al (1986). In addition, use of dihalogenated electrophiles for subunit activation generally requires that the 06 of guanine moieties is protected; this protection is achieved using the diphenylcarboamoyl group (Trichtinger).

Guanosine

In order to minimize side reactions during subunit activations it is often desirable to protect the guanine moiety on both the N2 and 06 using the procedure of Trichtinger et al (1983). The N-2 9-fluorenylmethoxycarbonyl derivative of guanosine is prepared by the procedure below which is general for the protection of nucleoside amino groups: guanosine (1 mmol) is suspended in pyridine (5 ml) and treated with trimethylchlorosilane (5 mmol). After the solution is stirred for 15 minutes, 9-fluorenylmethoxycarbonyl chloride (5 mmol) is added and the solution is maintained at room temperature for 3 hours. The reaction is cooled in an ice bath and water (1 ml) is added. After stirring for 5 minutes conc. ammonia (1 ml) is added, and the reaction is stirred for 15 minutes. The solution is evaporated to near dryness and the residue is dissolved in chloroform (10 ml). This solution is washed with sodium bicarbonate solution (5 ml, 10%), dried over sodium sulfate and evaporated. The residue is coevaporated several times with toluene and the product chromatographed on silica gel using a gradient of methanol in methylene chloride (0-50%).

N-2-Isobutyrylguanosine is prepared by the method of Letsinger.

N-2-acetylguanosine is obtained by the method of Reese.

N-2-naphthaylguanosine is prepared by the method of Dikshit; this reference provides a general method for the protection of nucleoside amine groups.

Adenosine

The N-6 2-(4-nitrophenyl)-ethoxycarbonyl derivative is prepared by the method of Himmelsbach.

N-6 (4-nitrobenzoyl)adenosine is prepared using the procedure above for FMOC-guanosine except that 4-nitrobenzoyl chloride is substituted for FMOC chloride.

The N-6 2-(phenylsulfonyl)-ethoxycarbonyl derivative is prepared by the procedure for FMOC guanosine except the 2-(phenylsulfonyl)-ethyl chloroformate (Balgobin) is used as the acylating agent and N-methylimidazole or pyridine is used as the solvent.

N-6 naphthoyladenosine is prepared by the method of Dikshit; this reference provides a general method for the protection of nucleoside amine groups.

2,6-diaminopurineriboside

The N-2,N-6-bis(9-fluorenylmethoxycarbonyl) derivative of 2,6-diaminopurine riboside is prepared by the general procedure described for guanosine.

The N-2,N-6-bis(isobutyryl) derivative is prepared by the general procedure described for guanosine.

Thioguanosine

The N-2(9-fluorenylmethoxycarbonyl) derivative of thioguanosine is prepared by the general procedure described for guanosine.

Uridine

To minimize undesired side products during the subunit activation step it is sometimes desirable to protect the $N_3$ of the uracil moiety. 5' O-tritylated uridine-2',3'-acetonide is converted to the N3 anisoyl derivative by the procedure of Kamimura et al (1983). The product is then treated with hot 80% acetic acid or 0.1 N HCl in THF to cleave the protective groups on the ribose moiety.

EXAMPLE 2

Synthesis of 5'-OH Morpholino Subunits

The steps in the method are illustrated in FIG. 5, with reference to structures shown in FIG. 5.

The base-protected ribonucleoside is oxidized with periodate to a 2'-3' - dialdehyde (Structure 1). The dialdehyde is closed on ammonia or primary amine (Structure 2) and the 2' and 3' hydroxyls (numbered as in the parent ribose) are removed by reduction with cyanoborohydride (Structure 3).

An example of this general synthetic scheme is described below with reference to the synthesis of a base-protected cytosine ($P_i^*$) morpholino subunit. To 1.6 l of methanol is added, with stirring, 0.1 mole of N-4-benzoylcytidine and 0.105 mole sodium periodate dissolved in 100 ml of water. After 5 minutes, 0.12 mole of ammonium biborate is added, and the mixture is stirred 1 hour at room temperature, chilled and filtered. To the filtrate is added 0.12 mole sodium cyanoborohydride. After 10 minutes, 0.20 mole of toluenesulfonic acid is added.

After another 30 minutes, another 0.20 mole of toluenesulfonic acid is added and the mixture is chilled and filtered. The solid precipitate is washed with two 500 ml portions of water and dried under vacuum to give the tosylate salt of the free amine shown in Structure 3.

The use of a moderately strong (pKa <3) aromatic acid, such as toluenesulfonic acid or 2-naphthalenesulfonic acid, provides ease of handling, significantly improved yields, and a high level of product purity.

The base-protected morpholino subunit is then protected at the annular nitrogen of the morpholino ring using trityl chloride or benzyhydral nitrophenyl carbonate (Structure 4). Alternatively, the 5' hydroxyl can be protected with a trialkylsilyl group.

As an example of a protection step, to 2 liters of acetonitrile is added, with stirring, 0.1 mole of the tosylate salt from above followed by 0.26 mole of triethylamine and 0.15 mole of trityl chloride. The mixture is covered and stirred for 1 hour at room temperature after which 100 ml methanol is added, followed by stirring for 15 minutes. After drying by rotovaping, 400 ml of methanol is added. After the solid is thoroughly suspended as a slurry, 5 liters of water is added, the mixture is stirred for 30 minutes and filtered. The solid is washed with 1 liter of water, filtered, and dried under vacuum. The solid is resuspended in 500 ml of dichloromethane, filtered, and rotovaped until precipitation just begins, after which 1 liter of hexane is added and stirred for 15 minutes. The solid is removed by filtering, and dried under vacuum.

The above procedure yields the base-protected morpholino subunit tritylated on the morpholino nitrogen and having a free 5' hydroxyl.

EXAMPLE 3

Alternative Synthesis of Morpholino Subunits

This example describes an alternative preparation of a morpholino subunit containing an acid-labile moiety linked to the morpholino ring nitrogen. The steps are described with respect to FIG. 6.

The subunit is prepared by oxidizing a ribonucleoside with periodate, as in Example 2, and closing the resultant dialdehyde (Structure 1) on the primary amine 4,4,-dimethoxybenzhydrylamine (which can be prepared by the method of Greenlee, 1984) buffered with benzotriazole, or p-nitrophenol. Reduction with sodium cyanoborohydride, carried out as in Example 2, gives a morpholino subunit (Structure 2) having a 4,4' -dimethoxybenzhydryl group on the morpholino nitrogen.

This procedure is particularly useful for preparing morpholino subunits from ribonucleosides which do not have a protective group on the base (e.g., uridine).

EXAMPLE 4

N-Sulfation of Morpholino Subunit

This example describes the preparation of a morpholino subunit protected on its 5' oxygen and sulfated on its morpholino ring nitrogen. The steps are described with reference to FIG. 12.

Structure 3 of FIG. 5 is silylated with t-butyldimethlsilyl chloride to give Structure 1 of FIG. 12. This product is then treated with $SO_3$/pyridine complex (with excess pyridine) in dimethylformamide (DMF) to give Structure 2 of FIG. 12.

It should be mentioned that the salts of sulfamic acids (e.g., Structure 7 of FIG. 5, and Structure 2 of FIG. 12)

and the salts of sulfonic acids (e.g., Structure 10 of FIG. 5, and Structure 5 of FIG. 7) can be easily chromatographed on silica gel using triethylamine/methanol/-chloroform mixtures if the silica is first pre-eluted with 2% triethylamine in chloroform.

EXAMPLE 5

Synthesis of 5'-Sulfamic Acid Morpholino Subunits

The steps in the synthesis of 5'-sulfamic acid morpholino subunits are described with reference to structures shown in FIG. 5.

The 5' hydroxyl of the doubly-protected morpholino subunit (Structure 4, FIG. 5) can be converted to the amine as follows. To 500 ml of DMSO is added 1.0 mole of pyridine (Pyr), 0.5 mole of triflouroacetic acid (TFA), and 0.1 mole of the morpholino subunit. The mixture is stirred until dissolved, and then 0.5 mole of diisopropylcarbodiimide (DIC) or dicyclohexylcarbodiimide (DCC) is added. After 2 hours the reaction mixture is added to 8 liters of rapidly stirred brine, which is stirred for 30 minutes and filtered. The solid is dried briefly, washed with 1 liter of ice cold hexanes, filtered, and the solid is added to 0.2 mole of sodium cyanoborohydride in 1 liter of methanol, stirred for 10 minutes, 0.4 mole of benzotriazole or p-nitrophenol is added, followed by 0.2 mole of methylamine (40% in $H_2O$) and the preparation is stirred four hours at room temperature [Note: the benzotriazole or p-nitrophenol buffers the reaction mixture to prevent racemization at the 4' carbon of the subunit at the iminium stage of the reductive alkylation]. Finally, the reaction mixture is poured into 5 liters of water, stirred until a good precipitate forms, and the solid (Structure 6, FIG. 5) is collected and dried. This dried product is next suspended in DMF and equivalents of $SO_3$/pyridine complex is added. Over a period of several hours, 8 equivalents of triethylamine is added dropwise with stirring. After an additional two hours the preparation is dumped into a large volume of brine and the solid collected by filtration and dried.

This sulfamic acid preparation is then purified by silica gel chromatography.

EXAMPLE 6

Synthesis of 5'-Sulfonate Morpholino Subunits

The steps in the synthesis of 5'-sulfonate morpholino subunits are described with reference to structures shown in FIG. 5.

For the following synthesis the morpholino nitrogen should be protected as a carbamate (e.g., Structure 4 of FIG. 5) instead of with a trityl group.

The 5' hydroxyl of the doubly-protected morpholino subunit is converted to a sulfhydral as follows. 0.1 mole of the 5'-hydroxyl subunit (Structure 4, FIG. 5) is added to 1 liter of pyridine followed by 0.12 mole of toluenesulfonylchloride, and stirred for 3 hours at room temperature to give Structure 8 of FIG. 5. After removing the pyridine by rotovapping, 0.5 mole of fresh sodium hydrosulfide in 1 liter of methanol/DMF containing NaI is added and the mixture is stirred at room temperature overnight. The reaction mix is added to 5 liters of water, stirred 20 minutes, and the solid material is collected by filtration and dried to give Structure 9 of FIG. 5. This sulfhydral product is next oxidized to the sulfonate (Structure 10 of FIG. 5) by dissolving in acetone or t-butanol/water mixture. Magnesium sulfate (0.2 mole) and potassium permanganate (0.5 mole) are added. The mixture is stirred at room temperature until reaction is complete, then filtered, and treated with excess aqueous $NaHSO_3$ to decompose $KMnO_4$ and $MnO_2$. The filtrate is partitioned between water containing triethylamine hydrochloride and chloroform. The chloroform layer is dried down and purified by silica gel chromatography to give Structure 10 of FIG. 5.

EXAMPLE 7

Synthesis of 5, Methylenesulfonate Subunit

This example describes the preparation of a subunit suitable for use in preparing polymers with 6-atom unit-length backbones having sulfonamide linkages.

For the preparation of subnits having Structure C of FIG. 3 wherein $X_2$, is $CH_2$, the starting material is the 5' aldehyde (Structure 5 of FIG. 5). This material is treated with phenyl diphenylphosphinylmethane sulfonate (Fild), then reduced with $H_2$/Pd on charcoal in a polar solvent, and lastly treated with alcoholic KOH in DMF. The product is reprotected on the morpholino nitrogen with trityl chloride and then purified by silica gel chromatography.

EXAMPLE 8

Preparation of 5'-aminomethanesulfonate Subunit

This example describes the preparation of a subunit suitable for use in preparing polymers with 7-atom unit-length backbones having sulfonamide linkages.

For the preparation of subnits having Structure D of FIG. 3 wherein $X_3$ is a methanesulfonated amine, the starting material is the 5' aldehyde (Structure 5 of FIG. 5). The 5' aldehyde is converted by reductive alkylation to a secondary amine by the method illustrated in Example 5, except that aminomethanesulfonic acid comprises the amine and ethylmorpholine is used to assure availability of the amine moiety for reaction with the aldehyde. This product is then reacted with methanesulfonyl chloride in the presence of triehtylamine to give the desired product, which is purified by silica gel chromatography.

EXAMPLE 9

Synthesis of N-methanesulfonate Subunit

This example describes the preparation of a subunit containing a sulfonate moiety linked to the morpholino ring nitrogen suitable for preparing polymers with 7-atom unit-length backbones. The steps are described with respect to structures shown in FIG. 7.

The subunit is prepared by oxidizing a ribonucleoside (Structure 1) with periodate in the presence of aminomethanesulfonic acid (AMSA) and N-ethyl morpholine. The oxidation is followed by reduction with sodium cyanoborohydride in the presence of benzotriazole (used to buffer the reaction mix) to give a morpholino subunit having a methane sulfonic acid group on the morpholino nitrogen (Structure 2).

The 5' hydroxyl (numbered as in the parent ribose) is then oxidized to an aldehyde (Structure 3) and converted to a primary or secondary amine (Structure 4) by reductive alkylation as in Example 5, and tritylated to give the desired subunit of Structure 5.

EXAMPLE 10

Preparation of N-methanecarboxylate Subunit

This example describes the preparation of a subunit containing a carboxylate moiety linked via a methylene to the morpholino ring nitrogen suitable for preparing polymers with 7-atom unit-length backbones.

The subnit can be prepared essentially as in Example 9, but substituting glycine for aminomethanesulfonic acid. Alternatively, it is generally more convenient to prepare it starting with Structure 3 of FIG. 5. This is readily alkylated on the morpholino ring nitrogen using chloroacetic acid or bromoacetic acid. The 5' hydroxyl is then converted to a primary amine and tritylated as in Example 9.

EXAMPLE 11

Synthesis of 5'-aminomethyl Riboside Subunit

N4-Benzoylcytidine-2',3'-acetonide (1 mmole) was converted to the 5'-Iodo derivative by reaction with methyltriphenoxyphosphonium iodide in DMF (20ml) under argon at room temperature for 20 hours. Methanol (5 ml) was added and after 30 minutes the mixture was evaporated in vacuo. The residue was dissolved in ethyl acetate and the solution washed with aqueous sodium thiosulfate, then brine. After drying with sodium sulfate and evaporation of the solvent the product was purified by chromatography on silica using isopropanol/chloroform mixtures.

The iodo compound (1 mmole) is reacted with potassium cyanide (5 mmol) in Dimethylsulfoxide for 12 hours under argon atmosphere. The nitrile is isolated by pouring the reaction mixture into saturated aqueous sodium dihydrogen phosphate. The mixture is extracted with ethyl acetate, the organic layer washed well with water, dried over sodium sulfate and evaporated in vacuo. The nitrile is purified by chromatography on silica using chloroform/ethylacetate mixtures.

The nitrile from the previous paragraph is treated with a mixture of equal parts of DMF and aqueous ammonia at 25° C. for 24 hours. The mixture is treated with rhodium on alumina and hydrogenated in a hydrogen atmosphere to provide the amine. After filtration and evaporation, the residue is dissolved in 0.2 N HCl to cleave the acetonide. After evaporation the amine diol may be purified by ion exchange on a cation exchange column. When appropriate, the amine moiety may be tritylated as in Example 2 to give the amine-protected 2',3'-diol.

EXAMPLE 12

Synthesis of 5'-aminoethylsulfonyl Riboside Subunit

2-Aminoethanethiol (2 mmol) is reacted with carbobenzoxychloride (1 mmol) in pyridine. The protected thiol carbamate is purified by $SiO_2$, using ethylacetate/hexane mixtures. Under an argon atmosphere the thiol (1 mmol) is dissolved in oxygen-free DMF containing 1.1 mmol oil-free sodium hydride. After evolution of gases the mixture is treated with the N4-benzoylcytidine-2' 3'-acetonide iodocompound from Example 11 (at 0° C.) and the mixture stirred at room temperature for 12 hours. The solvent was evaporated in vacuo. After redissolution in chloroform the solution was washed with sodium bicarbonate, then brine, then dried over $Na_2SO_4$, filtered and evaporated in vacuo. The residue was purified by chromatography on silica gel using chloroform/methanol mixtures.

The sulfide from the previous paragraph was oxidized with excess perbenzoic acid in chloroform to the sulfone. This was immediately treated with 0.2 N HCl/dioxane to cleave the acetonide group. The diol was purified by chromatography on silica using methanol/chloroform mixtures.

The diol sulfone from above is reduced with hydrogen/ palladium on carbon in DMF/methanol in the presence of acetic acid to remove the carbobenzoxy group. One equivalent of tosic acid is added to the mix, the solution is filtered and the filtrate evaporated. When appropriate the pendant amine is tritylated as in Example 2 to give the amine-protected 2',3'-diol If required, the benzoyl group on the base is removed by treatment with equal amounts of DMF and CMC aqueous ammonia at room temperature for 24 hours.

EXAMPLE 13

Activation and Coupling To Give Carbamate Linkage

This example describes the activation of morpholinosubunits, such as prepared in Example 2, and their subsequent coupling via a carbamate linkage to yield a 6-atom unit-length backbone. The example is described with reference to the Structures in FIG. 9.

Activation Step

Dry, N-protected, 5' hydroxyl morpholino nucleoside (Structure 1) (1 mmol), prepared as in Example 2, is treated with bis-(p-nitrophenyl)carbonate (BNPC) and triethylamine (TEA) in DMF under anhydrous conditions. The solution is stirred for three hours, then evaporated to dryness. The residue is dissolved in chloroform and chromatographed on silica gel eluting with an appropriate chloroform/methanol/0.1% TEA mixture to give activated subunit (Structure 2).

Deprotection Step 1.1 mmole morpholino nucleoside (Structure 1) is dissolved in 10 ml trifluoroethanol and 0.1 ml formic acid (or 0.2 ml acetic acid) added - giving a strong yellow color from the trityl carbonium ion - which fades on standing a few minutes. After five minutes the trifluoroethanol and acid are removed under reduced pressure and the deprotected subunit (Structure 3) resuspended in 5 ml DMF containing 0.5 ml triethylamine.

Coupling

The activated subunit (Structure 2) is added to the DMF solution of unprotected subunit and incubated at room temperature for 1 hour to give coupled product (Structure 4).

EXAMPLE 14

Activation of Sulfamic and Sulfonic Acids and Coupling to Give Sulfamide and Sulfonamide Linkages This example describes the activation of sulfamic acid salts (such as prepared in Examples 4 and 5) and the activation of sulfonic acid salts (such as prepared in Examples 6, 7, 8 and 9) and their coupling to form sulfamide and sulfonamide linkages, respectively. The example is described with reference to the structures in FIGS. 10 and 11.

Activation

Ten mmole of the triethylamine salt of sulfated subunit protected on the base and on the nitrogen of the morpholino ring (e.g., Structure 1 of FIGS. 10 and 11) is dissolved in 10 ml of dichloromethane and then 40 mmole of pyridine is added. This solution is chilled for 15 minutes on a bed of slowly added while the solution is rapidly stirred. After addition the solution is allowed to come to room temperature and then washed with aqueous $NaHCO_3$, dried, and chromatographed on silica gel eluted with a mixture of chloroform and acetone to give the desired sulfamoyl chloride (e.g., Structure 2 of FIG. 10) or sulfonyl chloride (e.g., Structure 2 of FIG. 11).

Deprotection

Eleven mmole of the triethylamine salt of sulfated subunit (e.g., Structure 1 of FIG. 10 or 11) is dissolved in 200 ml of trifluoroethanol and 0.2 ml of formic acid (or 0.4 ml acetic acid) added. After 5 minutes the solution is concentrated under reduced pressure and the deprotected subunit (e.g., Structure 3 of FIG. 10 or 11) precipitated with ether. The precipitate is then washed thoroughly with ether and then resuspended in 5 ml of DMF containing 0.6 ml of triethylamine. If an appreciable amount of residual formic or acetic acid remains in the deprotected subunit preparation the subsequent coupling efficiency can be seriously reduced. This reduction in efficiency is probably the result of the sulfamoyl chloride or sulfonyl chloride component reacting with these carboxylate salts to form mixed anhydrides, which in turn fail to react in the desired manner with the morpholino nitrogen of the deprotected component.

Coupling

The activated subunit (Structure 2) is added to the DMF solution of deprotected subunit (Structure 3) and incubated at room temperature for 1 hour to give coupled product (Structure 4).

EXAMPLE 15

Coupling of sulfamoyl Chloride with Alcohol to Give Sulfamate Linkage

This example describes the coupling of a sulfamoyl chloride (prepared as in Example 4 and activated as in Example 14) with a 5' hydroxyl subunit. This example is described with reference to the structures in FIG. 12.

One mmole of the sulfamoyl chloride, prepared as in Example 4 and activated as in Example 14 (Structure 3), 1 mmole 2,6-di-t-butyl-4-methylpyridine, 0.5 mmole of the alcohol component (Structure 4), and 20 ml of dry toluene are placed in an oven-dried round-bottom flask. After dissolution the reaction mixture is evaporated under reduced pressure and residual toluene removed under high vacuum. The residue is redissolved in methylene chloride (10 ml) and treated with silver trifluoromethanesulfonate (2 mmole). The reaction mixture is stirred at room temperature for several hours to complete cooling. Chloroform (20 ml) is added and the resulting milky suspension added to an acetonitrile solution (20 ml) of tetraethylammonium chloride (5 mmole). After stirring at room temperature for 30 minutes the excess solvent is removed by rotary evaporator, the residue dissolved in chloroform (150 ml) and filtered into a separatory funnel containing 0.05 N HCl (20 ml). Following over sodium sulfate, and then dried under vacuum. The residue is chromatographed on silica gel developed with a chloroform/methanol mixture to give the desired product (Structure 5).

EXAMPLE 16

Activation and Coupling To Give Amide Linkage

This example describes the activation of the carboxylate subunit prepared in Example 10 and coupling to form an amide linkage. The example is described with reference to the Structures in FIG. 13.

Activation 10 mmole of the subunit prepared in Example 10 (Structure 1) is dissolved in DMF containing 20 mmole of p-nitrophenol and 15 mmole of dicyclohexylcarbodiimide. After 1 hour the product is rotovaped and then purified by silica gel chromatography to give Structure 2.

Deprotection

Eleven mmole of the subunit prepared in Example 10 (Structure 1) is dissolved in 100 ml of dichloromethane, 1 ml of methanol and 1 ml of dichloroacetic acid. After 5 minutes the $CH_2Cl_2$, is removed under reduced pressure and the product washed with ether, dried and dissolved in 20 ml DMF containing 1 ml triethylamine to give Structure 3.

Coupling

The activated subunit (Structure 2) is added to the DMF solution of deprotected subunit (Structure 3) and incubated at room temperature for 1 hour to give coupled product (Structure 4).

EXAMPLE 17

Simultaneous Morpholino Ring Formation and Subunit Coupling

This example describes the oxidation of a ribonucleoside containing a protected amine linked through the 5' methylene, such as prepared in Example 11 or 12, and coupling to the unprotected amine of another subunit to simultaneously form a morpholino ring structure and join the subunits. The example is described with reference to the structures in FIG. 14.

Amine Protection

Ten mmole of ribonucleoside containing a 1° amine linked through the 5' methylene (Structure 1) is reacted with 11 mmole of trityl chloride to protect the amine (Structure 2).

Oxidation

Tritylated subunit (Structure 2), in methanol, is reacted with 11 mmole of $NaIO_4$ to give the dialdehyde (Structure 3).

Coupling

If the coupling solution is too acidic the reaction is very slow and if the solution is too basic epimerization of the Structure 3 component appears to occur. A weak acid is used to neutralize the amine component (Structure 1) and buffer the reaction in this coupling step. Weak acids which have been found suitable for this purpose are: carbonic, ortho and para nitrophenol, and benzotriazole. Accordingly, the dialdehyde (Structure 3) is combined with a suitable salt of Structure 1 in a water/methanol mixture to give the coupled product (Structure 4).

Reduction

Either during or after the morpholino ring closure step sodium cyanoborohydride is added to reduce the 2',3' dihydroxymorpholino ring (Structure 4) to the desired morpholino product (Structure 5).

EXAMPLE 18

Solution-Phase Block Assembly of Sulfamide-Linked Oligomer of the Sequence 5'= -CUGU This example describes the assembly of a short oligomer containing a sulfamide-linked backbone (Structure C—C of FIG. 4, wherein $X_2$, is a nitrogen) coupled as in Example 14. This solution assembly method is particularly useful for large-scale synthesis of short oligomers suitable for phase method (Example 19).

5' Sulfamic acid subunits of C, U, and G tritylated on the morpholino ring nitrogen are prepared as in Example 5. The U subunit is then activated by conversion to the sulfamoyl chloride form as in Example 14. The C subunit and the G subunit are deprotected as in Example 14. The deprotected C component (1.1 m mole) is dissolved in 5 ml DMF and 0.3 ml TEA, followed by addition of 1.0 m mole of the activated U component. Likewise, the deprotected G component is reacted with the activated U component.

After one hour each of these preparations is added to 100 ml of rapidly stirred brine and the solid collected and washed with water. The GU dimer is dried thoroughly under high vacuum and then activated as in Example 14. The best tetramer coupling results are obtained when purification of the dimer, via silica gel chromatography, is carried out after, rather than before, this activation step.

The CU dimer is deprotected as in Example 14. Better yields of tetramer are obtained when the dimer, after the initial ether precipitation, is thoroughly resuspended in about 2 ml of trifluoroethanol, reprecipitated with 30 ml of ether, and then resuspended in DMF and TEA for subsequent coupling.

Coupling to form the desired tetramer entails simply adding 1 m mole of activated GU dimer to the DMF/TEA solution containing 1.1 m mole of deprotected CU dimer.

Workup of the tetramer entails adding the reaction mixture to brine, washing the solid with water, and drying under vacuum to give the desired tetramer: 5' -CUGU having a sulfamic acid salt at the 5' end and a trityl on the morpholino nitrogen of the terminal U subunit. The structure of this tetramer is most easily confirmed by negative ion Fast Atom Bombardment mass spectroscopy. As a rule the dominant specie in the spectrum is the molecular ion.

EXAMPLE 19

Solid-Phase Assembly of Sulfamide-Linked Morpholino Polymer

This example describes the use of tetramer blocks, prepared as per Example 18, for solid-phase assembly of a morpholino polymer containing sulfamide intersubunit linkages. Solid-phase assembly provides a rapid method for assembly of longer binding polymers. The use of short oligomer blocks instead of monomers greatly simplifies separation of the final product from failure sequences.

A. Synthesis of short oligomers

The following tetramers are synthesized in solution: 5' -CUGU (Example 18); 5' -UCGG; 5' -GCGC; 5' -CACU. These tetramers are converted to their activated sulfomoyl chloride form by the general method described in Example 14.

B. Preparation of the first monomer with a cleavable linker and attachment to the solid support Morpholino C subunit containing a trityl moiety on the morpholino ring nitrogen and having a methylamine on the ' methylene, prepared as in Example 5, is reacted with a 3-fold molar excess of Bis[2-(succinimidooxycarbonyloxy)ethyl]sulfone from Pierce of Rockford, Ill, USA. This product is purified by silica gel chromatography and then added to a suitable solid support containing primary amine functions (e.g., Long Chain Alkyl Amine Controlled Pore Glass, from Pierce of Rockford, Ill). This procedure links the first tritylated subunit to the synthesis support via a linker which is stable to the acidic conditions used for detritylations, but which can be readily cleaved via a beta elimination mechanism using a strong non-nucleophilic base, such as a 1,8-Diazabicyclo[5.4.0]undec-7-ene (DBU).

C. Stepwise assembly of the polymer bound to the solid support

The coupling cycle for addition of each subunit or oligomer block generally includes deprotection of the terminal backbone moiety, a thorough wash, addition of the next activated subunit or oligomer block, and a thorough wash. The coupling efficiency for each addition can be determined by collecting each detritylation solution and subsequent wash and quantitating the trityl therein.

Detritylation in the present sufamide-linked polymer is achieved by slowly passing through the column a solution of 2% formic acid in trifluoroethanol (or 2% dichloroacetic acid in dicloromethane) until the eluant no longer tests positive for trityl (readily determined by adding a drop of eluant to 100 µl methanesulfonic acid and inspecting for the visible yellow color characteristic of the trityl carbonium ion). Thereafter the support is thoroughly washed to remove excess acid and then washed with DMF containing 1% by volume of N-ethylmorpholine (NEM). Coupling of the next subunit or oligomer block in the desired polymer sequence entails addition of a concentrated DMF solution containing the activated monomer or oligomer and a molar equivalent of NEM. Since the rate of coupling is a function of concentration it is desirable to add a substantial molar excess of monomer or oligomer relative to the concentration of support-bound growing chains. A 5-fold molar excess of activated monomer or oligomer over that of the growing chains often gives acceptable coupling efficiencies. Required coupling times can be determined by removing at specified time intervals small defined quantities of the support material, thoroughly washing, treating the support with methanesulfonic acid, and then spectrophotometrically quantitating the released trityl carbonium ion (molar absorbance at 409 nm is 45,000 in methane sulfonic acid). After coupling is complete the unreacted subunit or oligomer is washed from the support with DMF. The unreacted subunit is generally recovered, purified by chromatography, and reused for later synthesis. The support is thoroughly washed with the solvent trifluoroethanol, without added acid. Washing is complete when addition of a drop of the wash eluant to 100 μl methanesulfonic acid shows no yellow color.

The above coupling cycle is used to add, in order, the four activated tetramers 5'-CUGU; 5'-UCGG; 5'-GCGC; and 5'-CACU This results in the following polymer: support-linker-CCUGUUCGGGCGCCAUC-trityl.

D. Cleavage from the support

The synthesis support is treated with 20% DBU in DMF for two hours at room temperature in the presence of 2% diethylmalonate, to tie up the vinylsulfone generated during cleavage of the linker. The released morpholino polymer is washed from the support with DMF and precipitated by adding ethylacetate. The precipitate contains full-length polymer having a 5' methylamine, the bases still protected and a trityl moiety on the terminal morpholino nitrogen. In addition, the precipitate contains small amounts of failure sequences. At this stage the polymer size can be confirmed by positive ion fast atom mass spectrometry.

E. Addition of solubilizing moieties

If it is desired to add two solubilizing groups to the morpholino polymer this can be done conveniently by detritylting the N-terminal morpholino nitrogen using 2% formic acid in trifluoroethanol. Alternatively, if only one solubilizing moiety is to be added, then the 5' methylamine is acetylated with acetic anhydride before the detritylation step.

Polyethylene glycol 1000 (from Polysciences Inc., Warrington, Pa, USA) is thoroughly dried by dissolving in dry DMF and then evaporating the solvent under vacuum. The solid is resuspended in a minimal volume of pure dry DMF and 0.5 mole equivalent (relative to PEG 1000) of bis(p-nitrophenyl)carbonate and 1 mole equivalent of TEA is added and the preparation sealed and incubated overnight at 30° C. to give p-nitrophenyl carbonate-activated PEG 1000.

The full-length morpholino polymer which has been detritylated is added to a substantial molar excess (generally 10- to 20-fold) of activated PEG 1000 and incubated two hours at room temperature. Unreacted PEG 1000 is removed by precipitation of the tailed polymer with ether.

F. Base deprotection

The dried polymer is suspended in DMSO, the DMSO solution chilled, and an equal volume of concentrated NH4OH is carefully layered on top of the chilled DMSO, and the container tightly capped. The preparation is incubated at 30° C. for eighteen hours. Thereafter, the solution is briefly exposed to aspirator vacuum to remove ammonia.

G. Purification of morpholino polymer

Purification at pH 2.5 is general for binding polymers wherein about half or more of the base-pairing moieties are of types 1, 2, 3, and 7 of FIG. 2.

Water to be used for chromatography is degassed under aspirator vacuum and phosphoric acid added to give pH 2.5 (solvent A). A corresponding pH 2.5 solution is made 2 N in KCl (solvent B). Solvent A is mixed 1:1 by volume with chromatographic-grade acetonitrile to give solvent C.

Load up to about 10 mg of this polymer in 10 ml of solvent A on a chromatography column 1 cm in diameter and 10 to 20 cm in length which is packed with the cation-exchange support S-Sepharose Fast Flow (Pharmacia). Proportionately larger quantities can be loaded on larger columns of the same length, e.g., up to 60 mg can be loaded on a 2.5 cm diameter column and 250 mg on a 5 cm diameter column. After washing the column thorough with solvent A elute with a linear gradient ranging from 100% solvent A to 100% solvent B and monitor the eluant to 254 nm. The desired binding polymer is generally the last and the largest peak to elute from the column. When the polymer is prepared by block assembly, base-line separations are often achieved. When peak shapes are unsymmetrical the problem generally has been due to insolubility of the binding polymer rather than a lack of capacity of the chromatographic packing. Such a problem, which is most common when the binding polymers do not contain a solubilizing moiety, can often be solved by reducing the quantity of binding polymer loaded in a given run. When peaks are symmetrical but base-line separation is not achieved, substantial improvements are usually attained simply by eluting with a shallower gradient.

The eluant containing the polymer is desalted by loading on an equivalent-sized column packed with 35 micron chromatographic polypropylene (Cat. No. 4342 from Polysciences, Inc.) and washing thoroughly with solvent A. If baseline separation was achieved in the foregoing cation exchange chromatography, then pure product is obtained simply by eluting with solvent C; otherwise, the product is eluted with a linear gradient ranging from 100% solvent A to 100% solvent C. When the product is somewhat acid sensitive the solution is neutralized with dilute NaOH before drying under reduced pressure.

Purification at high pH

Purification at pH 11 is generally used for binding polymers wherein above half or more of the base-pairing moieties are at type 4, 5, 6 and 9 of FIG. 2.

N,N-diethylethanolamine (Aldrich) is added to degassed water to adjust the pH to 11.0 (solvent D). A corresponding pH 11 solution 2 N in KCl (solvent E) is prepared. A third pH 11 solution is prepared by mixing Solvent D 1:1 by volume with chromatographic grade acetonitrile (solvent F).

The fully-deprotected binding polymer, prepared as above, is suspended in solvent D at a concentration of about 1 mg/ml. The pH is adjusted, if necessary, to pH 11 with N,N-diethylethanol-amine. About 10 ml of this polymer solution is placed on a chromatography column 1 cm in diameter and 10 to 20 cm in length which is packed with anion-exchange support Q-Sepharose Fast Flow (Pharmacia). After washing the column thoroughly with solvent D, the column is eluted with a linear gradient ranging from 100% solvent D to 100% solvent E and the eluant is monitored at 254 nm.

The eluant containing the polymer is desalted by loading on an equivalent-sized column of polypropylene and washing thoroughly with solvent D. If baseline separation is achieved in the foregoing anion exchange chromatography then pure product is obtained simply by eluting with solvent F; otherwise, the product is eluted with a linear gradient ranging from 100% solvent D to 100% solvent F. Fractions containing the product are dried under reduced pressure.

H. Sequence confirmation

While mass spectral analysis of the full-length polymer in the fully-protected state, as described earlier, does serve to confirm both the polymer length and the base composition, it does not provide information on the subunit sequence. Significant sequence information can be obtained from fragmentation patterns of deoxyribonucleic acids and carbamate-linked deoxyribonucleoside-derived polymers (Griffin et al. (1987), Biomed. & Environ. Mass Spectrometry 17:105); however, many of the morpholino polymers of the instant invention are quite resistant to fragmentation and give predominantly the molecular ion with only minimal fragments.

One method for confirming the sequence of the polymer is to take a small portion of the growing polymer after coupling each oligomer block and use mass spectral analysis to follow the elongation of the polymer. This method is applicable except for those rare cases where two blocks used in the synthesis happen to have exactly the same mass.

An indirect method to help verify the correctness of the polymer subunit sequence is to pair the morpholino polymer with its complementary DNA (whose sequence can be confirmed by established methods) and with DNA sequences which might have resulted if the blocks were assembled in the wrong order. Pairing between the polymer and DNA can be evaluated by the occurrence of a hypochromic shift in the 240 to 290 nm wavelength region; such a shift occurs only between the polymer and its complementary sequence. The polymer/DNA duplex can also be distinguished from any partially-mismatched duplex by slowly raising the temperature while monitoring the absorbance in the 240 to 290 nm wavelength region. The perfect duplex will have a melting temperature (corresponding to a 50% reduction in the hypochromicity) generally 10 degrees or more above that of any mismatched duplex.

EXAMPLE 20

Solution-Phase Assembly of Simple Prototype Morpholino Polymer, Structural Confirmation, Deprotection, Purification, and Assessment of Binding to Target DNA Sequence This example describes the preparation, structural confirmation, and assessment of target binding affinity of a simple carbamate-linked morpholino polymer.

A carbamate-linked morpholino hexamer wherein all $P_i$ moieties are cytosines is assembled from dimer prepared as in Example 13. One third of that dimer preparation is detritylated (as in Example 13) and the remaining two thirds is activated (again as in Example 13). Half of the activated dimer is reacted with the detritylated dimer to give tetramer, which is purified by silica gel chromatography developed with 6% methanol/94%chloroform. The tetramer is detritylated and reacted with the remaining activated dimer to give hexamer, which is purified by silica gel chromatography developed with 10% methanol/90% chloroform.

This carbamate-linked =' OH, base-protected hexamer having a trityl moiety on the morpholino nitrogen is designated c(mC*)$_6$-trityl. Photon NMR gives:

$\delta = 8.25$–7.90 (18H, m), 7.65–7.05 (39H, m), 6.16 (1H, bd), 5.77 (4H, m), 5.69 (1H, bd), 4.46 (1H, m), 4.35–3.80 (25H, m), 3.56 (2H, m), 3.25–2.75 (12H, m), 1.47)1, m), 1.24 (1H, m).

The mass spectrum (3-nitrobenzyl alcohol matrix) shows:

M-1 = 2352.6 (2), 459.2 (30), 306.2 (100).

The high-resolution mass spectrum shows an M-1 of 2352.8197, which is in good agreement for Cphd 120H$_{112}$N$_{24}$O$_{29}$calculated as 2352.8026.

This c(mC*)$_6$-trityl polymer is next detritylated as in Example 13, and then a polyethylene glycol 1000 tail is added followed by base deprotection, as in Example 19. Purification is by cation exchange chromatography followed by desalting on a column of polypropylene, as described in Example 19.

This purified tailed hexamer, c(mC*)$_6$-PEG1000, shows an absorption maximum at 267.1 nm in neutral aqueous solution, with a calculated molar absorbance of 42,800. In aqueous solution at pH 1, the same material shows an absorption maximum at 275.7 nm, with a calculated molar absorbance of 77,100. Proton NMR data for this final product is as follows:

$\delta = 7.74$ (6H, broad d), 5.97 (6H, broad D), 5.65 (6H, broad D), 4.30–4.05 (12H, m), 4.04–3.80 (18H, m), a large envelope containing the PEG protons, and several signals of the oligomer, 2.99–2.80 (120H, m).

To assess target binding affinity 20 A$_{260}$ units of DNA target p(dG)$_6$, purchased from Pharmacia LKB, is dissolved in 50 microliters of deionized water and 200 microliters of DMSO (spectrophotometric grade from Aldrich Chem. Co.) is added (stock solution A). 1.8 mg of the tailed morpholino hexamer, c(mC)$_6$-PEG1000, is dissolved in 0.36 ml of spectrophotometric grade DMSO (stock solution B). Phosphate buffer is prepared by adjusting the pH of 0.05 N NaOH to 7.4 using phosphoric acid, followed by addition of EDTA to a final concentration of 0.001 N (Buffer C).

Stock solutions A and B are assayed for the actual concentration of polymer by UV; the absorbance of stock solution A is measured in 0.1 N NaOH and stock solution B is measured in 0.1 N HCl. Measurements at these pH extremes minimize base stacking and other polymer interactions which can give absorbance values not proportional to the component monomers. Stock solutions A and B are diluted with Buffer C to give solutions of a final concentration of 10 micromolar in polymer. The required dilutions are calculated using molar absorbencies of 65,000 for solution A, p(dG)6, and 77,100 for solution B, c(mC*)$_6$-PEG1000.

Assessment of target binding affinity is carried out in a double-beam scanning spectrophotometer having a temperature-controlled cell housing which will accommodate two cells in the reference beam and two in the sample beam.

Using four matched quartz cuvettes, one is filled with 0.5 ml of 10 micromolar p(dG)$_6$ and 0.5 ml of Buffer C and a second is filled with 0.5 ml of 10 micromolar c(mC*)$_6$-PEG1000 and 0.5 ml of Buffer C. These two cuvettes are placed in the reference beam of the temperature-controlled cell housing. Next, a third cuvette is filled with 1 ml of Buffer C and a fourth is filled with 0.5 ml of 10 micromolar p(dG)$_6$ and 0.5 ml of 10 micromolar c(mC*)$_6$-PEG1000. These two cuvettes are placed in the sample beam of the cell housing. The cell housing is then heated to 60° C. and allowed to cool slowly to 14° C. to assure complete pairing between the polymer and its DNA target in the fourth cuvette. A scan is then taken from 320 nm to 240 nm —which shows a substantial absorbance difference due to a hypochromic shift in polymer-target mixture, centered around 273 nm. The temperature of the cell holder is then raised in 2-degree increments to 80° C., with scans taken after each 2-degree rise.

For comparison, the same procedure is used for assessing the binding affinity of p(dC)$_6$ DNA for its target p(dG)$_6$, which gives a similar but less intense hypochromic shift in the paired state.

Figure 15:
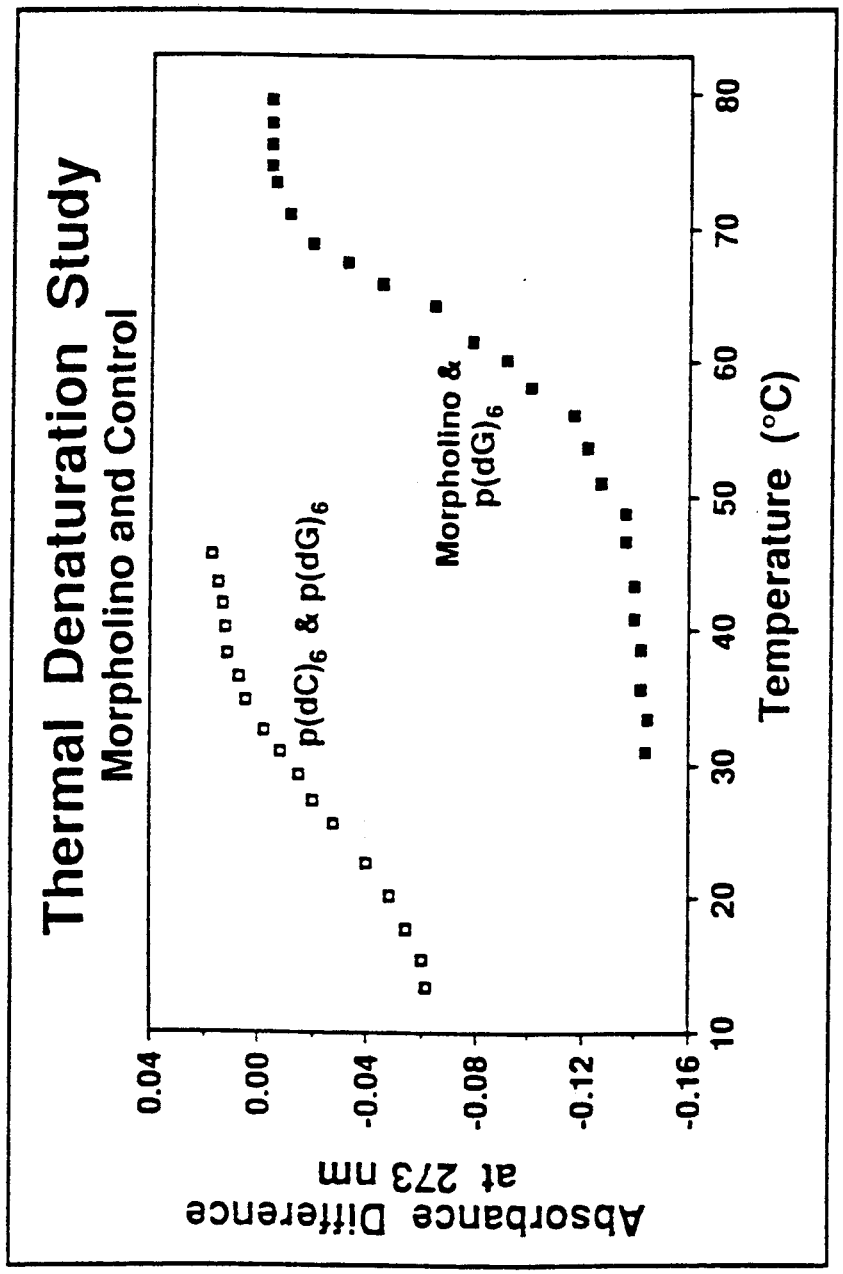
FIG. 15 shows thermal denaturation plots for poly(dC)/poly(dG) and poly(C morpholino)/poly(dG) duplexes where the poly(C morpholino) was constructed according to the present invention.

Plots of the absorbance difference as a function of temperature for both the morpholino polymer/DNA and the analogous DNA/DNA complexes are shown in FIG. 15. The melting temperature, $T_m$, wherein the complex is half melted, is seen to be 62° C. for the morpholino polymer/DNA and 30° C. for the DNA/DNA. At low salt concentrations such as used here, the charge repulsion between the anionic DNA backbones substantially destabilizes the DNA/DNA duplex, while there is no corresponding electrostatic repulsion between the morpholino polymer and its DNA target.

EXAMPLE 21

Solution-phase Assembly of Simple Prototype Sulfamide-linked Morpholino Polymer and Assessment of Binding to RNA and DNA Target Sequences This example describes the preparation and target binding of a simple sulfamide-linked morpholino polymer.

A sulfamide-linked morpholino hexamer, wherein all $P_i$ moieties are cytosines, is assembled from 5' sulfated methylamine subunit (R is methyl) prepared as in Example 5 and activated as in Example 14. Activated monomer is reacted in DMF with an excess of 5' OH subunit lacking a protective group on the morpholino nitrogen, prepared as in Example 2. The resultant dimer is purified by silica gel chromatography developed with methanol/chloroform mixtures and then deprotected as in Example 14. This product is then reacted with more activated monomer, the chain-extended product purified, and deprotected as above. This cycle is repeated until hexamer is obtained.

Before the last detritylation, the mass of the hexamer was confirmed by negative ion FAB mass spectroscopy, which showed M-1 = 2598.9 (100).

As in Example 20, the sulfamide-linked hexamer is tailed with PEG-1000, deprotected, purified, and tested for binding to its DNA target, p(dG)$_6$, and its RNA target, poly(G). The target-binding affinities, expressed in $T_m$ values, for this sulfamide-linked hexamer, referred to as s(mC)$_6$, are tabulated below, along with the corresponding target-binding affinities for the analogous DNA oligomer, p(dC)$_6$.

|  | $T_m$ value (°C.) |
| --- | --- |
| s(mC)$_6$/p(dG)$_6$ | 25 |
| p(dC)$_6$/p(dG)$_6$ | 29 |
| s(mC)$_6$/poly(G) | 33 |
| s(dC)$_6$/poly(G) | 38 |

While specific embodiments, methods, and uses of the invention have been described, it will be appreciated that various changes and modifications of the invention may be made without departing from the invention. In particular, although preferred polymer backbone structures have been described and illustrated, it will be appreciated that other morpholino-based polymers may be constructed according to the backbone constraints and requirements discussed above.

It is claimed:

1. A polymer composition comprised of morpholino subunit structures of the form:

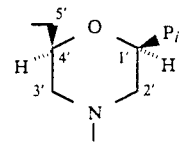

where (i) the structures are linked together by uncharged, achiral linkages, one to three atoms long, joining the morpholino nitrogen of one subunit to the 5', exocyclic carbon of an adjacent subunit, and (ii) $P_i$ is a purine or pyrimidine base-pairing moiety effective to bind by base-specific hydrogen bonding to a base in a polynucleotide.

2. The composition of claim 1, wherein $P_i$ is selected from the group consisting of:

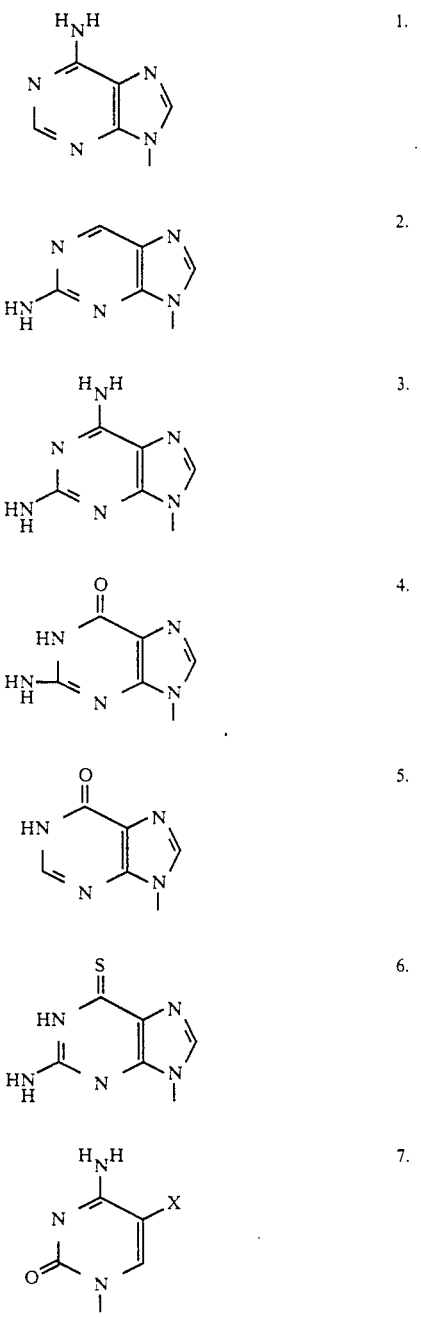

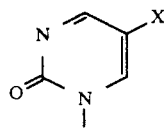

and

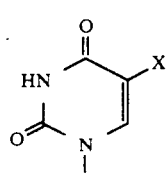

where X is H, CH₃, F, Cl, Br, or I.

3. The composition of claim 1, wherein the linked structures have a form selected from the group consisting of:

(A)

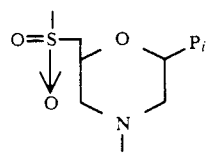

(B)

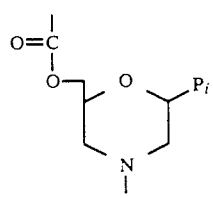

(C)

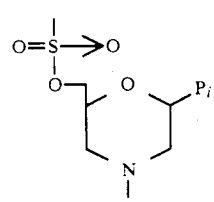

(D)

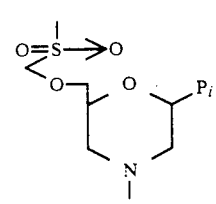

(E)

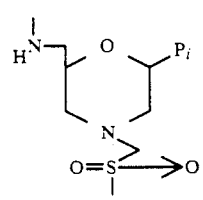

(F)

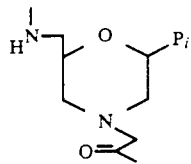

and (G)

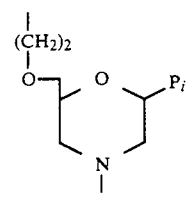

4. The composition of claim 1, wherein the linkage is of the form:

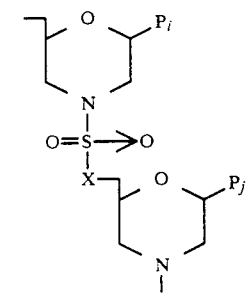

where $P_iX$ is NH, NCH₃, O, S, or CH₂; and, $P_1$ is a purine or pyrimidine base-pairing moiety effective to bind by base-specific hydrogen bonding to a base in a polynucleotide.

5. The composition of claim 1, wherein the linkage is of the form:

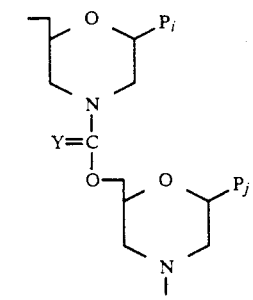

where $P_iY$ is O or S; and, $P_i$ is a purine or pyrimidine base-pairing moiety effective to bind by base-specific hydrogen bonding to a base in a polynucleotide.

6. The composition of claim 1, wherein the linkage is of the form:

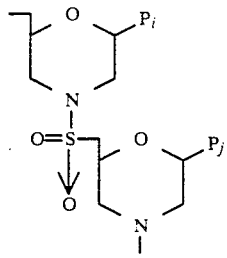

where $P_i$ is a purine or pyrimidine base-pairing moiety effective to bind by base-specific hydrogen bonding to a base in a polynucleotide.

7. The composition of claim 1, wherein the linkage is of the form

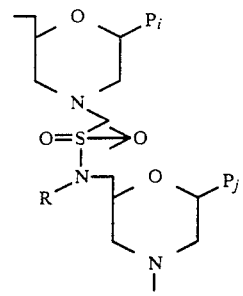

where $P_i R$ is H or $CH_3$; and,
$P_i$ is a purine or pyrimidine base-pairing moiety effective to bind by base-specific hydrogen bonding to a base in a polynucleotide.

8. The composition of claim 1, which further includes a moiety at one or both termini which is effective to enhance the solubility of the polymer in aqueous medium.

9. The composition of claim 7, wherein the terminal moiety is polyethylene glycol.

10. The composition of claim 1, composed of at least 3 morpholino subunits.

11. The composition of claim 1, wherein at least one of the $P_i$ is a 2,6-diaminopurine.

12. The composition of claim 1, wherein at least one of the $P_i$ is a 5-halouracil.

13. The composition of claim 1, wherein at least of 70% of the $P_i$ are 2-amine containing purines.

* * * * *